United States Patent
Levy et al.

(10) Patent No.: US 7,332,280 B2
(45) Date of Patent: Feb. 19, 2008

(54) CLASSIFICATION OF PATIENTS HAVING DIFFUSE LARGE B-CELL LYMPHOMA BASED UPON GENE EXPRESSION

(76) Inventors: Ronald Levy, 966 Means Ct., Stanford, CA (US) 94305; Mark A. Wechser, 850 Lincoln Centre Dr., Foster City, CA (US) 94404; Izidore S. Lossos, 1475 NW. 12th Ave. (D8-4), Miami, FL (US) 33136; Robert J. Tibshirani, 580 St Claire Dr., Palo Alto, CA (US) 94306; Ash A. Alizadeh, 328 Greenfield Ave., San Mateo, CA (US) 94403; David Botstein, 253 Christopher Dr., Princeton, NJ (US) 08540

(*) Notice: Subject to any disclaimer, the term of this patent is extended or adjusted under 35 U.S.C. 154(b) by 207 days.

(21) Appl. No.: 10/792,374

(22) Filed: Mar. 3, 2004

(65) Prior Publication Data

US 2005/0079513 A1    Apr. 14, 2005

Related U.S. Application Data

(60) Provisional application No. 60/510,822, filed on Oct. 14, 2003.

(51) Int. Cl.
  C12Q 1/68    (2006.01)
  G01N 33/574  (2006.01)
  G01N 33/48   (2006.01)

(52) U.S. Cl. ................ 435/6; 435/7.23; 435/6; 436/64

(58) Field of Classification Search ........... 435/7.23, 435/6; 536/23.1
See application file for complete search history.

(56) References Cited

U.S. PATENT DOCUMENTS

| | | |
|---|---|---|
| 4,586,546 A | 5/1986 | Mezei et al. |
| 5,561,058 A | 10/1996 | Gelfand et al. |
| 5,618,703 A | 4/1997 | Gelfand et al. |
| 5,693,517 A | 12/1997 | Gelfand et al. |
| 5,876,978 A | 3/1999 | Willey et al. |
| 5,916,524 A | 6/1999 | Tisone |
| 5,998,768 A | 12/1999 | Hunter et al. |
| 5,999,209 A | 12/1999 | Hunter et al. |
| 6,005,664 A | 12/1999 | Korenberg et al. |
| 6,036,920 A | 3/2000 | Pantoliano et al. |

(Continued)

OTHER PUBLICATIONS

Robetorye et al., J of Molecular Diagnostics, vol. 4, pp. 123-136, Aug. 2002.*

(Continued)

*Primary Examiner*—Shanon Foley
*Assistant Examiner*—Lei Yao
(74) *Attorney, Agent, or Firm*—Harness, Dickey & Pierce, P.L.C.

(57) ABSTRACT

Methods and kits for classifying patients having diffuse large B-cell lymphoma (DLBCL) based upon expression of a plurality of genes are disclosed. Real-time quantitative RT-PCR can be used to measure expression values. Correlating expression values of the plurality of genes in a tumor sample from the patient to reference expression values obtained from DLBCL patients can stratify patients in the classification groups. The methods and kits can be used to predict overall patient survival.

11 Claims, 4 Drawing Sheets

U.S. PATENT DOCUMENTS

| | | | |
|---|---|---|---|
| 6,037,129 A | 3/2000 | Cole et al. | |
| 6,087,098 A | 7/2000 | McKiernan et al. | |
| 6,088,100 A | 7/2000 | Brenan et al. | |
| 6,154,707 A | 11/2000 | Livak et al. | |
| 6,203,759 B1 | 3/2001 | Pelc et al. | |
| 6,214,293 B1 | 4/2001 | Pantoliano et al. | |
| 6,235,520 B1 | 5/2001 | Dehlinger et al. | |
| 6,300,073 B1 | 10/2001 | Zhao et al. | |
| 6,309,608 B1 | 10/2001 | Zhou et al. | |
| 6,358,679 B1 | 3/2002 | Heid et al. | |
| 6,373,726 B1 | 4/2002 | Russell | |
| 6,406,891 B1 | 6/2002 | Legerski | |
| 6,436,677 B1 | 8/2002 | Gu et al. | |
| 6,448,089 B1 | 9/2002 | Vuong | |
| 6,472,218 B1 | 10/2002 | Stylli et al. | |
| 6,485,917 B1 | 11/2002 | Yamamoto et al. | |
| 6,586,257 B1 | 7/2003 | Vuong | |
| 6,638,483 B2 | 10/2003 | Vuong | |
| 6,730,883 B2 | 5/2004 | Brown et al. | |
| 6,814,933 B2 | 11/2004 | Vuong | |
| 6,825,927 B2 | 11/2004 | Goldman et al. | |
| 6,852,986 B1 | 2/2005 | Lee et al. | |
| 2001/0049134 A1 | 12/2001 | Lee et al. | |
| 2002/0090320 A1 | 7/2002 | Burrow et al. | |
| 2002/0098593 A1 | 7/2002 | Nelson et al. | |
| 2002/0098598 A1 | 7/2002 | Coffen et al. | |
| 2002/0111742 A1* | 8/2002 | Rocke et al. | 702/19 |
| 2003/0027179 A1 | 2/2003 | Heid et al. | |
| 2003/0060439 A1* | 3/2003 | Goldberg et al. | 514/44 |
| 2003/0087446 A1 | 5/2003 | Eggers | |
| 2003/0108868 A1 | 6/2003 | Richards | |
| 2003/0109060 A1 | 6/2003 | Cook et al. | |
| 2003/0118483 A1 | 6/2003 | Militzer et al. | |
| 2003/0124539 A1 | 7/2003 | Warrington et al. | |
| 2003/0136921 A1 | 7/2003 | Reel | |
| 2003/0179639 A1 | 9/2003 | Stolakis et al. | |
| 2003/0190652 A1 | 10/2003 | De La Vega et al. | |
| 2003/0202637 A1 | 10/2003 | Yang | |
| 2003/0205681 A1 | 11/2003 | Modlin | |
| 2003/0207464 A1 | 11/2003 | Lemmo et al. | |
| 2003/0215957 A1 | 11/2003 | Lemmo et al. | |
| 2003/0219760 A1* | 11/2003 | Gordon et al. | 435/6 |
| 2004/0014238 A1 | 1/2004 | Krug et al. | |
| 2004/0018506 A1 | 1/2004 | Koehler et al. | |
| 2004/0057870 A1 | 3/2004 | Isaksson et al. | |
| 2004/0061071 A1 | 4/2004 | Dorsel | |
| 2004/0131505 A1 | 7/2004 | Koeda | |
| 2004/0202577 A1 | 10/2004 | McNeil et al. | |
| 2004/0203047 A1 | 10/2004 | Caren et al. | |
| 2004/0203164 A1 | 10/2004 | Cizdziel et al. | |

OTHER PUBLICATIONS de Vos et al., Lab Invest , vol. 83, pp. 271-285, Feb. 2003.*
A. Alizadeh, M. Eisen et al., Distinct types of diffuse large B-cell lymphoma identified by gene expression profiling Nature vol. 403, p. 503, Feb. 2000.*
A. Rosenwald, G. Wright et al., The Use of Molecular Profiling to Predict Survival After Chemotherapy for Diffuse Large-B-Cell Lymphoma N Engl J Med, vol. 346, No. 25, Jun. 2002.*
Adida et al., *Prognostic significance of surviving expression in diffuse large B-cell lymphomas*, Blood, vol. 96, No. 5, pp. 1921-1925, 2000.
Alizedeh et al., *Distinct Types of Diffuse Large B-cell Lymphoma Identified by Gene Expression Profiling*, Nature, vol. 403, pp. 503-511, 2000.
Barrans et al., *Germinal center phenotype and bcl1-2 expression combined with the International Prognostic Index improves patient risk stratification in diffuse large B-cell lymphoma*, Blood, vol. 99, No. 4, pp. 1136-1143, 2002.

Boehm et al., *The rhombotin family of cysteine-rich LIM-domain oncogenes: Distinct members are involved in T-cell translocations to human chromosomes 11p15 and 11p13*, Proc. Natl. Acad. Sci. U S A, vol. 88, No. 10, pp. 4367-4371, 1991.
Cattoretti et al., *BCL-6 Protein Is Expressed in Germinal-Center B Cells*, Blood, vol. 86, No. 1, pp. 45-53, 1995.
Chang et al., *BCL-6, a POZ/zinc-finger protein, is a sequence-specific transcriptional repressor*, Proc. Natl. Acad. Sci. U S A, vol. 93, pp. 6947-6952, 1996.
Dent et al., *T helper type 2 inflammatory disease in the absence of interleukin 4 and transcription factor STAT6*, Proc. Natl. Acad. Sci. U S A, vol. 95, pp. 13823-13828, 1998.
Freeman et al., *Quantitative RT-PCR: Pitfalls and Potential*, BioTechniques, vol. 26, No. 1, pp. 112-125, 1999.
Gascoyne et al., *Prognostic Significance of Bcl-2 Protein Expression and Bcl-2 Gene Rearrangement in Diffuse Aggressive Non-Hodgkin's Lymphoma*, Blood, vol. 90, No. 1, pp. 244-251, 1997.
Harris et al., *A Revised European-American Classification of Lymphoid Neoplasms: A Proposal From the International Lymphoma Study Group*, Blood, vol. 84, No. 5, pp. 1361-1392, 1994.
Hermine et al., *Prognostic Significance of bcl-2 protein Expression in Aggressive Non-Hodgkin's Lymphoma*Blood, vol. 87, No. 1, pp. 265-272, 1996.
Hill et al., *Prognostic Significance of BCL-2 Expression and bcl-2 Major Breakpoint Region Rearrangement in Diffuse Large cell Non-Hodgkin's Lymphoma: A British National Lymphoma Investigation Study*, Blood, vol. 88, No. 3, pp. 1046-1051, 1996.
Ichikawa et al., *Mutations of the p53 Gene as a Prognostic Factor in Aggressive B-Cell Lymphoma*, New England J Med, vol. 337, No. 8, pp. 529-534, 1997.
Kaiser, *Seeking the Cause of Induced Leukemias in X-SCID Trial*, Science, vol. 299, p. 495, 2003.
Kerckaert et al., *LAZ3, a novel zinc-finger encoding gene, is disrupted by recurring chromosome 3q27 translocations in human lymphomas*, Nat. Genet, vol. 5, pp. 66-70, 1993.
Koduru et al., *Correlation Between Mutation in P53, p53 Expression, Cytogenetics, Histologic Type, and Survival in Patients With B-Cell Non-Hodgkin's Lymphoma*, Blood, vol. 90, No. 10, pp. 4078-4091, 1997.
Kramer et al., *Clinical Relevance of BCL2, BCL6, and MYC Rearrangements in Diffuse Large B-Cell Lymphoma*, Blood, vol. 92, No. 9, pp. 3152-3162, 1998.
Kramer et al., *Clinical Significance of bcl2 and p53 Protein Expression in Diffuse Large B-Cell Lymphoma: A Population-Based Study*, J. Clin Onco, vol. 14, No. 7, pp. 2131-2138, 1996.
Krenacs et al., *Transcription Factor B-Cell-Specific Activator Protein (BSAP) is Differentially Expressed in B Cells and in Subsets of B-Cell Lymphomas*, Blood, vol. 92, No. 4, pp. 1308-1316, 1998.
Livak et al., *Analysis of Relative Gene Expression Data Using Real-Time Quantitative PCR and the $2^{-\Delta\Delta c_T}$ Method*, Methods, vol. 25, pp. 402-408, 2001.
Lossos et al., *HGAL is a novel interleukin-4-inducible gene that strongly predicts survival in diffuse large B-cell lymphoma*, Blood, vol. 101, No. 2, pp. 433-440, 2003.
Lossos et al. *Expression of a single gene, BCL-6, strongly predicts survival in patients with diffuse large B-cell lymphoma*, Blood, vol. 98, No. 4, pp. 945-951, 2001.
Lossos et al., *Diffuse Large B-Cell Lymphoma: Insights Gained from Gene Expression Profiling*, Int. J. Hematol., vol. 77, pp. 321-329, 2003.
Lossos et al., *Optimization of quantitative real-time RT-PCR parameters for the study of lymphoid malignancies*, Leukemia, vol. 17, pp. 789-795, 2003.
Miller et al., *Prognostic Significance of the Ki-67-Associated Proliferative Antigen in Aggressive Non-Hodgkin's Lymphomas: A Prospective Southwest Oncology Group Trial*, Blood, vol. 83, No. 6, pp. 1460-1466, 1994.
Pfaffl et al., *Relative expression software tool (REST ©) for group-wise comparison and statistical analysis of relative expression results in real-time PCR*, Nucleic Acid Research, vol. 30, No. 9, e36, pp. 1-10, 2002.

Royer-Pokora et al., *TTG-2, a new gene encoding a cystein-rich protein with the LIM motif, is overexpressed in acute T-cell leukaemia with the t(11;14) (p13;q11)* Oncogene, vol. 6, pp. 1887-1893, 1893.

Proost et al., *The Role of Chemokines in Inflammation*, Int. J. Clin. Lab. Res., vol. 26, pp. 211-223, 1996.

Rosenwald et al., *The use of molecular profiling to predict survival after chemotherapy for diffuse large-B-Cell lymphoma*, N. Engl. J. Med., vol. 346, No. 25, pp. 1937-1947, 2002.

Seyfert et al., *Transcriptional repression by the proto-oncogene BCL-6*, Oncogene, vol. 12, pp. 2331-2342, 1996.

Shaffer et al., *BCL-6 Represses Genes that Function in Lymphocyte Differentiation, Inflammation, and Cell Cycle Control*, Immunity, vol. 13, pp. 199-212, 2000.

Shipp et al., *Diffuse large B-cell lymphoma outcome prediction by gene-expression profiling and supervised machine lerarning*, Nat. Med., vol. 8, No. 1, pp. 68-74, 2002.

Terol et al., *Soluble intercellular adhesion molecule-1 (s-ICAM-1/s/CD54) in diffuse large B-cell lymphoma: association with clinical characteristics and outcome*, Ann Oncol, vol. 14, pp. 467-474, 2003.

Shipp et al., *A Predictive Model For Aggressive Non-Hodgkin's Lymphoma*, The International Non-Hodgkin's Lymphoma Prognostic Factors Project, *New England Journal Med.*, vol. 329, No. 14, pp. 987-994, 1993.

The Non-Hodgkin's Lymphoma classification Project, *A Clinical Evaluation of the International Lymphoma Study Group Classification of Non-Hodgkin's Lymphoma*, Blood, vol. 89, No. 11, pp. 3909-3918, 1997.

Tusher et al., *Significance analysis of microarrays applied to the ionizing radiation response*, Proc. Natl. Acad. Sci. U S A, vol. 98, No. 9, pp. 5116-5121, 2001.

Warren et al., *The Oncogenic Cysteine-Rich LIM Domain Protein Rbtn2 Is Essential for Erythroid Development*, Cell, vol. 78, pp. 45-57, 1994.

Yamada et al., *The oncogenic LIM-only transcription factor Lmo2 regulates angiogenesis but not vasculogenesis in mice*, Proc. Natl. Acad. Sci. U S A, vol. 97, No. 1, pp. 320-324, 2000.

Ye et al., *The BCL-6 proto-oncogene controls germinal-centre formation and Th2-type inflammation*, Nat. Genet., vol. 16, pp. 161-170, 1997.

Drillenburg, P. et al.; CD44 expression predicts disease outcome in localized large B cell lymphoma; Leukemia; pp. 1448-1455; (1999).

Hans, C.P. et al.; "Confirmation of the molecular classification of diffuse large B-cell lymphoma by imunohistochemistry using a tissue microarray"; Blood; vol. 103, No. 1; Sep. 22, 2003; pp. 275-282.

Lossos, I.S. et al.; "Prediction of survival in diffuse large B-cell lymphoma based on the expression of six genes"; The New England Journal of Medicine; vol. 350, No. 18; Apr. 29, 2004; pp. 1828-1837.

Wright, G. et al.; "A gene expression based method to diagnose clinically distinct subgroups of diffuse large B cell lymphoma"; Proceedings of the National Academy of Sciences of the United States of America; vol. 100, No. 17, Aug. 19, 2003.

* cited by examiner

CLASSIFICATION OF PATIENTS HAVING DIFFUSE LARGE B-CELL LYMPHOMA BASED UPON GENE EXPRESSION

CROSS-REFERENCE TO RELATED APPLICATIONS

This application claims the benefit of U.S. Provisional Application No. 60/510,822, filed on Oct. 14, 2003, which is hereby incorporated in its entirety by reference.

GOVERNMENT INTERESTS

The present inventions may have been made with support from the U.S. Government under U.S.P.H.S. Grants CA33399 and CA34233, awarded by the National Institutes of Health. The present inventions may have been made with support from the U.S. Government under NIST Grant No. 70NANB8H4002. The U.S. Government may have certain rights in the inventions recited herein.

FIELD

This application relates generally to gene expression in cancerous tissues and, more particularly, to gene expression in diffuse large B-cell lymphoma (DLBCL) tissues and to methods for classifying patients with DLBCL based upon gene expression in DLBCL tissues.

BACKGROUND

Although combination chemotherapy for the treatment of DLBCL patients has been available for several years, currently, over one-half of all patients do not achieve a durable remission (Vose, supra, 1998). Risk stratification of patients has been attempted to identify patients in which more aggressive treatment may be required. One risk stratification approach has involved use of the International Prognostic Index (IPI), which is based upon 5 clinical criteria (The International Non-Hodgkin's Lymphoma Prognostic Factors Project, *N. Engl. J. Med.* 32:987-993, 1993). However, the IPI has not provided an accurate prediction of survival in a substantial number of patients.

SUMMARY

Accordingly, the present inventors have succeeded in developing an approach for stratifying DLBCL patients at the molecular level based upon gene expression in DLBCL tissues. The approach involves correlating expression values of a plurality of genes in tumor samples from patients having DLBCL to classification characteristics of the disease, such as, for example, overall patient survival. A set of genes can be selected from the plurality of genes based upon the expression of the selected genes showing a correlation to the classification characteristics. The relationship developed from this correlation can then allow patient classification by measuring expression of the selected genes in a tumor sample from a patient and comparing with expression values obtained in the correlation study. The approach can be applied not only to DLBCL, but also to other cancers as well as non-cancerous diseases.

Thus, in various embodiments, the present invention can involve methods for classifying a patient or patients having DLBCL into groups based upon classification characteristics. The methods can comprise measuring expression of a plurality of genes, in a tumor sample from a patient and correlating tumor expression values to normalized reference expression values obtained for the plurality of genes from DLBCL patients stratified in the classification groups. In various aspects of this embodiment, the method can predict patient survival based upon the selected plurality of genes being predictive of survival by virtue of being identified in DLBCL patients stratified in groups of known overall survival. In various aspects of this embodiment as well as embodiments described below, classification characteristics other than or in addition to overall survival can be used such as, for example, likelihood of successful treatment for various treatments which can be used to select a specific therapy approach for a given patient. Gene expression can be measured by any method that quantifies gene expression such as real time RT-PCR. Quantification can be relative or absolute quantification or a combination of both as applied to the normalization process, which is discussed more fully below. Briefly, relative quantification references expression of a target gene to a control value for expression such as, for example, expression obtained from a control sample or pretreatment sample or expression of a reference gene. Absolute quantification is based upon an internal or external calibration curve (see for example, Pfaff et al., *Nucleic Acid Research* 30:e36, 2002; Livak et al., *Methods* 25:402-408, 2001).

In various other embodiments, the present invention can involve a method for obtaining a formula for classifying patients having a disease, such as, for example, DLBCL. The method comprises correlating normalized expression values of a plurality of genes in tumor samples obtained from patients having the disease to at least one known classification characteristic of the disease. In various aspects of this embodiment, the method can predict patient survival and the classification characteristic of the disease can be overall survival. Gene expression can be measured by any method which quantitates gene expression such as real time RT-PCR. The plurality of genes can be at least two, at least three, at least four, at least five or all of the genes LMO2, BCL-6, FN1, CCND2, SCYA3 and BCL-2. Additional genes can also be included.

The present invention, in various embodiments, can also involve kits for classifying a patient having DLBCL into classification groups, such as, for example, groups predictive of the probability of survival of the patient. The kits contain assays for measuring expression of a plurality of genes in a tumor sample from a patient having DLBCL. The normalized expression of the plurality of genes in tumor samples from DLBCL patients stratifies the patients into classification groups. The assays in the kits can comprise real time RT-PCR assays. The kits can also contain software for using the expression data so as to simplify the assignment of patients to classification groups.

In various embodiments, the present invention can also involve a method for predicting survival in a patient having DLBCL. The method comprises measuring in a sample containing tumor cells from the patient, expression of a plurality of genes and determining whether normalized expression of the genes indicates increased or decreased probability of survival. The plurality of genes can be at least three, at least four, at least five or all of the genes LMO2, BCL-6, FN1, CCND2, SCYA3 and BCL-2. Additional genes can also be included. In one aspect, determining can involve determining whether normalized expression of the three or more genes matches expression criteria indicative of increased probability of survival, compared to expression in reference cells. The reference cells can be non-cancerous cells from the patient or cells other than DLBCL tumor cells obtained from sources other than the patient such as, for example, Raji cells. The expression criteria can be selected from the group consisting of increased expression of LMO2, increased expression of BCL-6, increased expression of FN1, decreased expression of CCND2, decreased expression of SCYA3 and decreased expression of BCL-2. In various aspects of this embodiment, the reference cells can be Raji cells. Gene expression can be measured by any of a number of methods such as, for example, cDNA or cRNA microarray test, tissue microarray test or real time RT-PCR.

In various of the embodiments above, normalized expression can comprise values calculated by one or both of calculating the ratio of expression values of the target gene and an endogenous reference gene and calculating the ratio of expression values of the target gene to expression of the same gene reference cells with or without normalization to the endogenous reference gene. The endogenous reference gene can be a housekeeping gene such as, for example, PGK1 or GAPDH. The reference cell line can be a Raji cell line. Reference stratification of patients based upon expression values can be generated using univariate Cox proportional hazards analysis with classification, such as, for example, overall survival as dependent variable. Moreover, the methods can use IPI scores in addition to the gene expression information obtained.

In various of the embodiments above, gene expression in a patient can be compared to gene expression in reference DLBCL patients of known survival using the formula:

$$Z=(A \times LMO2)+(B \times BCL6)+(C \times FN1)+(D \times CCND2)+(E \times SCYA3)+(F \times BCL2)$$

The terms LMO2, BCL6, FN1, CCND2, SCYA3 and BCL2 can be log base 2 of normalized expression values for genes LMO2, BCL-6, FN1, CCND2, SCYA3 and BCL-2, respectively. In various embodiments A can be about −0.03, B can be about −0.2, C can be about −0.2, D can be about 0.03, E can be about 0.2 and F can be about 0.6. Using these values, a Z value of less than about −0.06 can indicate high probability of survival, a Z value of from about −0.06 to about 0.09 can indicate medium probability of survival and a Z value of greater than about 0.09 can indicate low probability of survival. In various aspects of this embodiment, A can be about −0.0273, B is about −0.2103, C can be about −0.1878, D can be about 0.0346, E can be about 0.1888 and F is can be about 0.5527. Using these values, a Z value of less than about −0.063 indicates high probability of survival, a Z value of from about −0.063 to about 0.093 indicates medium probability of survival and a Z value of greater than about 0.093 indicates low probability of survival.

Application of the methods of the present invention to clinical practice allows identification of patients who are unlikely to be cured by conventional therapy and in whom investigational approaches would be justified in an effort to improve their outcome.

DETAILED DESCRIPTION

Figure 1:
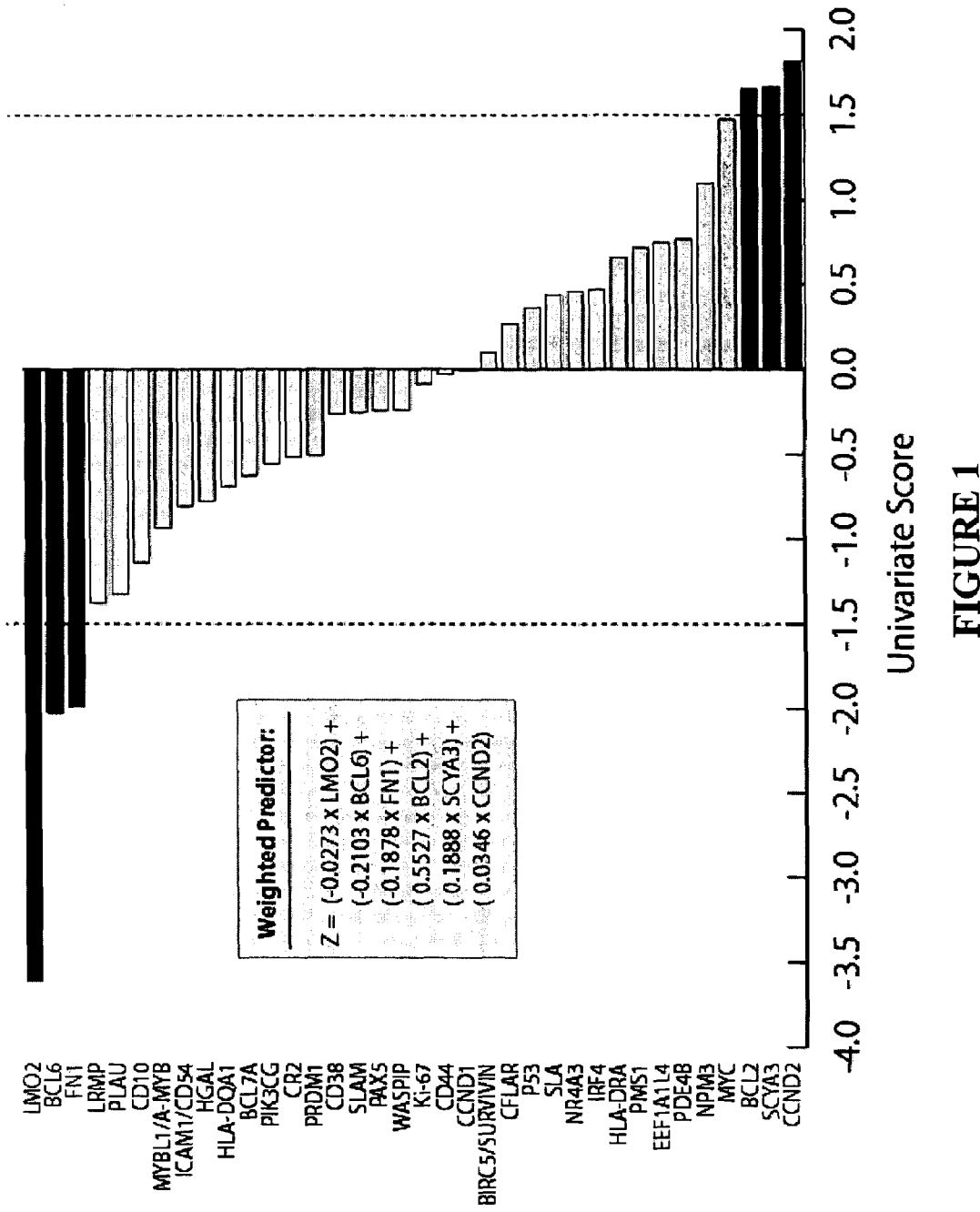
FIG. 1 illustrates univariate analysis of expression of 36 genes using overall survival as a dependent variable, wherein the genes are ranked based on their predictive power (univariate score) with negative score associated with longer overall survival while positive univariate score associated with shorter overall survival, the dashed lines (at a univariate score of 1.5) representing a significance threshold of $p<0.05$.

The present invention, in various embodiments, can involve methods for classifying patients having a disease into groups based upon gene expression values from a plurality of genes. The disease can be DLBCL or other cancers or a non-cancerous disease.

Classification groups or stratification groups for patients having DLBCL can involve any of a variety of features of the disease, in particular, various aspects that characterize the severity of the disease into groups based upon morbidity or mortality of the patients having the disease. One measure of mortality is "overall survival" sometimes referred to as "survival rate". The term "overall survival" refers to the percentage of subjects in a study who have survived for a defined period of time, usually measured from the time of diagnosis although it can also be measured from the time of initiation of treatment. Overall survival time of DLBCL patients as referenced herein, is calculated from the date of the diagnosis until death or last follow-up examination.

Inasmuch as DLBCL patients normally receive various treatments for the disease, overall survival time can mean survival time following chemotherapy. Chemotherapy can be Anthracycline-based chemotherapy and such anthracycline-based chemotherapy, as used herein, is intended to refer to the use of at least one anthracycline-class compound in chemotherapy treatment. As a non-limiting example, doxirubicin is an anthracycline-class compound used for treating non-Hodgkin's lymphoma and this compound can be used in a combination treatment of cyclophosphamide, doxorubicin, vincristine and prednisone (Vose, supra, 1998).

In various embodiments, the disease DLBCL can be identified in patients prior to applying the methods of the present invention. Methods of diagnosing DLBCL are well known in the art such as, for example, the use of histologic and immunologic criteria (see for example, Harris et al, *Blood* 84:1361-1392, 1994; The Non-Hodgkin's Lymphoma classification Project, *Blood* 89:3909-3918, 1997). After identification, the methods of the present invention can be used to classify patients having the disease.

In various embodiments, the methods of the present invention can also be used in determining whether DLBCL is present in a patient and in distinguishing of DLBCL from other diseases as well as in monitoring of the disease status or the recurrence of the disease, and in determining a preferred therapeutic regimen for the patient. Gene expression in DLBCL tumors can thus, be used in the diagnosis of DLBCL patients. Assessing the gene expression profile of DLBCL tumors can, in certain instances, provide a diagnostic basis for identifying disease aggressiveness and tumor progression (Lossos et al, *Int. J. Hematol.* 77:321-329, 2003). Thus, in various embodiments, classification of patients into survival probability groups can constitute the classification of patients into subsets of DLBCL diseases having different clinical prognoses.

Identification of patterns of gene expression can form the basis for understanding tumorigenesis at the molecular level as well as the underlying mechanisms that may contribute to disease aggressiveness and tumor progression (Lossos et al., *Int. J. Hematol.* 77:L321-329, 2003). Thus, evaluation of gene expression related to DLBCL can provide a more meaningful approach to understanding the disease than has been available in histologic or other clinical tests that have attempted to classify patients with DLBCL. Gene expression involves transcription of genomic DNA to form RNA's and ultimately proteins in the cell. Assessing gene expression can be done by determining cellular RNA or protein levels in a cell. Numerous methods for measuring gene expression at the RNA or protein level are known. Non-limiting examples of methods that measure RNA include Northern blotting, nuclease protection assays, DNA microarrays, serial analysis of gene expression, quantitative reverse transcription-polymerase chain reaction (RT-PCR), differential-display RT-PCR, massively parallel signature sequencing and the like. In particular, measurement of gene expression at the RNA level can be performed using real-time quantitative RT-PCR assay such as exonuclease-based assays, for example, TaqMan® assays. Non-limiting examples of methods of measuring protein expression levels include mass spectrometry, two-dimensional gel electrophoresis, antibody microarrays, tissue microarrays, ELISA, radioimmunoassay, immuno-PCR and the like.

In various embodiments, the methods of the present invention can be used to identify the pattern of gene expression in DLBCL and to determine the relationship to various aspects of DLBCL such as, for example, disease prognosis. A number of genes have been suggested to be related to DLBCL (see for example Alizedeh et al., *Nature* 403:503-511, 2000; Shipp et al., supra, 2002; Rosenwald, et al., supra, 2002 and Table 1 below). These and other genes can be evaluated using various methods of the present invention to assess the relationship of gene expression to disease prognosis such as overall survival in a population of individuals having DLBCL and to determine the prognosis of an individual having the disease. In particular, BCL-6 has been shown to predict survival in DLBCL patients using real-time RT-PCR methods (Lossos et al., *Blood* 98:945-951, 2001). Thus, in various embodiments, BCL-6 can be one of the genes used to classify DLBCL patients in overall survival groups.

In various embodiments gene expression values can be normalized to provide more accurate quantification and to correct for experimental variations. In various aspects of the invention, the calculation of gene expression values from the real-time RT-PCR tests can involve generating $C_t$ (threshold cycle) values for target gene and an endogenous reference gene RNAs from control and experimental samples; determining nanogram amounts of each RNA using calibration standard curves; calculating the ratio of target and endogenous gene reference RNA; and calculating the ratio of nanograms target gene RNA in control and experiment samples. The endogenous reference RNA can be that of a housekeeping gene (see for example, Lossos et al, *Leukemia* 17:789-795, 2003). In particular, phosphoglycerate kinase 1 (PGK1) or glyceraldehyde-3-phosphate dehydrogenase (GAPDH) can be used as the endogenous reference RNA. Calibration standard curves can be generated using cDNA from Raji cells or from Universal Human Reference RNA (Stratogene, La Jolla, Calif.). Raji cells can also be used for determining control target gene RNA and endogenous gene RNA. Normalization aspects of the calculations can comprise one or both of calculating the ratio of expression values of the target gene and an endogenous reference gene and calculating the ratio of expression values of the target gene to expression of the same gene in a reference cell line with or without normalization to the endogenous reference gene. Other normalization methods that correct for experimental variation can also be used (for review see Freeman et al, *BioTechniques* 26:112-125, 1999).

The normalized gene expression values can be transformed to log-base 2 values. Further evaluation can then be performed by comparing the transformed values with selected classification criteria using various statistical methods. In constructing a survival prediction model, the normalized gene expression can be compared to overall survival as estimated using the product-limit method of Kaplan-Meier with comparisons based upon the log-rank test. Cox proportional hazards analysis with overall survival as the dependent variable can then be performed. Genes with an absolute univariate Cox score between −1.5 and 1.5 can then be analyzed by multivariate regressions analysis using a Cox proportional hazards regression model with overall survival as the dependent variable.

The invention can be further understood by reference to the examples which follow.

EXAMPLE 1

This example illustrates the selection of genes potentially predictive of overall survival and the performance of quantitative RT-PCR on the selected genes.

Thirty-six genes were selected for inclusion in the study as shown in Table 1.

TABLE 1

Sources of supporting evidence for panel of 36 prognostic genes assessed in this study

| Genes (total = 36 total)[†] | Reference |
|---|---|
| ICAM1/CD54 | Terol et al., Ann Oncol 14: 467-74, 2003. |
| PAX5 | Krenacs et al., Blood 92: 1308-16, 1998 |
| Ki-67 | Miller et al., Blood 83: 1460-6, 1994 |
| CD44 | Drillenburg et al., Leukemia 13: 1448-55, 1999 |
| P53 | Ichikawa et al., N Engl J Med 337: 529-34, 1997; Koduru et al., Blood 90: 4078-91, 1997 |
| BCL-2 | Gascoyne, et al, Blood 90: 244-51, 1997; Kramer et al., J Clin Onco 14: 2131-8, 1996; Hermine et al., Blood 87: 265-72, 1996; Hill et al., Blood 88: 1046-51, 1996 |
| BIRC5/SURVIVIN | Adida et al., Blood 96: 1921-5, 2000 |
| BCL-6 | Lossos et al., Blood 98: 945-951, 2001; Barrans et al., Blood 99: 1136-43, 2002 |
| PRDMI | Shaffer et al., Immunity 13: 199-212, 2000 |
| HGAL | Lossos et al., Blood 101: 433-40, 2003 |
| SCYA3 | Shaffer et al., Immunity 13: 199-212, 2000 |
| SCYA3 | Shaffer et al., Immunity 13: 199-212, 2000 |
| CCND1 | Shaffer et al., Immunity 13: 199-212, 2000 |
| CCND2 | Shaffer et al., Immunity 13: 199-212, 2000 |
| LMO2, LRMP, CD10, MYBL1/A-MYB, BCL7A, PIK3CG, CR2, CD38, SLAM, WASPIP, CFLAR, SLA, IRF4, PMS1, HGAL, BCL-6, BCL-2 | Alizadeh et al., Nature 403: 503-11, 2003[††] |
| NR4A3, PDE4B | Shipp et al. Nat Med 8: 68-74, 2002 |

TABLE 1-continued

Sources of supporting evidence for panel of 36 prognostic genes assessed in this study

| Genes (total = 36 total)[†] | Reference |
|---|---|
| FN1, PLAU, HLA-DQA1, HLA-DRA, EEF1A1L4, NPM3, MYC, BCL-6, HGAL | Rosenwald et al., N Engl J Med 346: 1937-47, 2002 |

[†]Some of the genes are present in more than one source and are thus repeated in the table. We also included three genes that are known targets of BCL-6 (PRDM1, SCYA3, CCND2) based on work by Shaffer et al, given the prominence of BCL-6 in DLBCL.
[††]In addition to representatives from the ~71 genes employed by Alizadeh et al, we also included genes based on a reanalysis of the dataset using SAM.

The expression of each of these had previously been reported to predict DLBCL survival, either in single gene studies or in the analysis of large data sets derived from microarray studies. In addition, we applied Significance Analysis of Microarrays (Tusher et al., *Proc Natl Acad Sci USA* 98:5116-21, 2001)—a supervised method for the identification of genes significantly associated with survival—to the dataset of Alizadeh et al. (Alizadeh et al., supra, 2000), to detect and recover any significant genes missed in the exploratory analyses employed by the authors.

Tumor specimens from patients newly diagnosed with DLBCL were obtained during the course of diagnostic procedures at Stanford University medical center between the years of 1975 and 1995. Specimens were stored as previously reported. All the DLBCL tumors had the histological appearance of centroblastic large cell lymphomas demonstrating diffuse pattern of involvement without evidence of residual follicles. All patients were treated with an anthracycline containing chemotherapy regimen and had clinical follow up at Stanford University Hospital. A total of 66 primary DLBCL specimens fulfilled these inclusion criteria. Staging information was obtained for all the patients according to the Ann Arbor system. The IPI score was able to be determined for 59 of these patients.

For each of these 36 genes and a pair of internal controls for input mRNA (PGK1 and GAPDH), we measured gene expression using quantitative RT-PCR, based on primer and probe sets shown in Table 2. We assayed the expression of each gene in each of the 66 patient specimens relative to that in a reference RNA sample. Isolation of RNA, its quantification and the RT reactions were performed as previously reported (Lossos et al., *Blood* 101:433-40, 2003; Lossos et al., *Leukemia* 17:789-95, 2003).

TABLE 2

Primer and probe sequences employed for panel of 36 genes surveyed.

| Gene | Accession No. (Assay I.D. No.)* | Sequences | | SEQ. ID. NO. |
|---|---|---|---|---|
| ICAM1/ | NM_000201 | Probe | CTGTTCCCAGGACCTG | 1 |
| CD54 | (Hs00277001_m1) | Forward Primer | ACGCTGAGCTCCTCTGCTACTC | 2 |
| | | Reverse Primer | CACAGATGTCTGGGCATTGC | 3 |
| PMS1 | NM_000534 | Probe | CATAGTTCTCCAGTTTAAC | 4 |
| | (Hs00153333_m1) | Forward Primer | TGGATGCTGGTGCCACAA | 5 |
| | | Reverse Primer | CGTTATCTCGCACCTCAATTTTATC | 6 |

TABLE 2-continued

Primer and probe sequences employed for panel of 36 genes surveyed.

| Gene | Accession No. (Assay I.D. No.)* | | Sequences | SEQ. ID. NO. |
|---|---|---|---|---|
| p53/TP53 | NM_000546 | Probe | CTGGCTGCCAATCC | 7 |
| | (Hs00153340_m1) | Forward Primer | GCTTTCCACGACGGTGACA | 8 |
| | | Reverse Primer | TGACTGCGGCTCCTCCAT | 9 |
| BCL2 | NM_000633 | Probe | ACAAAGGCATCCCAGCC | 10 |
| | (Hs00153350_m1) | Forward Primer | ACCTGCACACCTGGATCCA | 11 |
| | | Reverse Primer | ACAGCCAGGAGAAATCAAACAGA | 12 |
| BIRC5/ | NM_001168 | Probe | CCTTTGCAATTTTG | 13 |
| SURVIVIN | (Hs00153353_m1) | Forward Primer | CTGGACAGAGAAAGAGCCAAGAA | 14 |
| | | Reverse Primer | GGCACGGCGCACTTTCT | 15 |
| PRDM1 | NM_001198 | Probe | TGAATCTCACACAAACAC | 16 |
| | (Hs00153357_m1) | Forward Primer | CCCGGAGAGCTGACAATGA | 17 |
| | | Reverse Primer | TCAGTGCTCGGTTGCTTTAGACT | 18 |
| BCL6 | NM_001706 | Probe | CCTTACCATTGTGAGAAGT | 19 |
| | (Hs00277037_m1) | Forward Primer | GCGAATCCACACAGGAGAGAA | 20 |
| | | Reverse Primer | TTGTGACGGAAATGCAGGTTAC | 21 |
| CCND1/ | NM_001758 | Probe | TCCATTTGCAGCAGCT | 22 |
| PRAD1 | (Hs00277039_m1) | Forward Primer | CCGAGAAGCTGTGCATCTACAC | 23 |
| | | Reverse Primer | AGGTTCCACTTGAGCTTGTTCAC | 24 |
| CCND2 | NM_001759 | Probe | ACAGACCTCCAGCATC | 25 |
| | (Hs00277041_m1) | Forward Primer | CCCTACATGCGCAGAATGGT | 26 |
| | | Reverse Primer | GACCTCTTCTTCGCACTTCTGTTC | 27 |
| CD38 | NM_001775 | Probe | CTTCTGCAAACCTGC | 28 |
| | (Hs00277045_m1) | Forward Primer | GGAGAAAGGACTGCAGCAACA | 29 |
| | | Reverse Primer | AGCATCACATGGACCACATCAC | 30 |
| CR2 | NM_001877 | Probe | AGGCACACACCAGTTT | 31 |
| | (Hs00153398_m1) | Forward Primer | CCAGCCAGCTGATCAGAAGAC | 32 |
| | | Reverse Primer | TCCGCTGAATTCCAAGCAAT | 33 |
| Ki-67 | NM_002417 | Probe | CACTCTCATCAGGGTCAG | 34 |
| | (Hs00267195_m1) | Forward Primer | CGTCGTGTCTCAAGATCTAGCTTCT | 35 |
| | | Reverse Primer | GGACACACGCCTTCTTTTCAA | 36 |
| IRF4 | NM_002460 | Probe | CCCAGCAGGTTCAC | 37 |
| | (Hs00277069_m1) | Forward Primer | CTACACCATGACAACGCCTTACC | 38 |
| | | Reverse Primer | GGCTGATCCGGGACGTAGT | 39 |
| MYC | NM_002467 | Probe | TCCTCCTCAGAGTCGC | 40 |
| | (Hs00153408_m1) | Forward Primer | CCCCTGGTGCTCCATGAG | 41 |
| | | Reverse Primer | GCCTGCCTCTTTTCCACAGA | 42 |

TABLE 2-continued

Primer and probe sequences employed for panel of 36 genes surveyed.

| Gene | Accession No. (Assay I.D. No.)* | | Sequences | SEQ. ID. NO. |
|---|---|---|---|---|
| PDE4B | NM_002600 | Probe | TCGCATTCAGGTCCTT | 43 |
| | (Hs00277080_m1) | Forward Primer | CAGGCGTTCTTCTCCTAGACAACTA | 44 |
| | | Reverse Primer | GGTCTGCACAGTGTACCATGTTG | 45 |
| PIK3CG | NM_002649 | Probe | ATGTCCTGAAATTTC | 46 |
| | (Hs00277090_m1) | Forward Primer | GGAAAGAAGACAAGCCCACACTT | 47 |
| | | Reverse Primer | GTGATGACGAAGGGCTAGATAAGC | 48 |
| SCYA3/ CCL3 | NM_002983 | Probe | CTGCATCACTTGCTGC | 49 |
| | (Hs00234142_m1) | Forward Primer | ATGGCTCTCTGCAACCAGTTCT | 50 |
| | | Reverse Primer | GCGGTCGGCGTGTCA | 51 |
| SLAM | NM_003037 | Probe | ACCTGCTCATAAAGC | 52 |
| | (Hs00234150_m1) | Forward Primer | CGCTTTTGCCTGCAGTTGA | 53 |
| | | Reverse Primer | CGTTCTCCTGGGTCTTGTTTAAAA | 54 |
| WASPIP | NM_003387 | Probe | CTCCAGAATCATTATCC | 55 |
| | (Hs00277097_m1) | Forward Primer | TGAGATCCACGGCCAACAG | 56 |
| | | Reverse Primer | CTCCCGGTGGCAACAATG | 57 |
| CFLAR | NM_003879 | Probe | AGACAGAGCTTCTTCG | 58 |
| | (Hs00153439_m1) | Forward Primer | TGCCTGATAATCGATTGCATTG | 59 |
| | | Reverse Primer | CCCAGGGAAGTGAAGGTGTCT | 60 |
| LMO2 | NM_005574 | Probe | AGACTATCTCAGGCTTTT | 61 |
| | (Hs00277106_m1) | Forward Primer | CAAACTGGGCCGGAAGCT | 62 |
| | | Reverse Primer | ATGCGCAGAGACCGTCTTG | 63 |
| LRMP | NM_006152 | Probe | AAAGCTTCTTCAGTTTCC | 64 |
| | (Hs00277107_m1) | Forward Primer | GCCAGGCACTTCAGCAGAA | 65 |
| | | Reverse Primer | GGACAGGGAATCATAGTGAGGAAAT | 66 |
| SLA | NM_006748 | Probe | CCTGCAGTCTGGACAC | 67 |
| | (Hs00277129_m1) | Forward Primer | TCACCTTGCGTCAGAAGACTGT | 68 |
| | | Reverse Primer | CCCAAGCGGGTTCTCTGTT | 69 |
| NR4A3 | NM_006981 | Probe | CATGATCACAGAAAGAC | 70 |
| | Hs00175077_m1 | Forward Primer | GCCTGCCTGTCAGCACTGA | 71 |
| | | Reverse Primer | GCTCTTCGACTCTCTTTGGTTCTTT | 72 |
| CD10 | NM_007289 | Probe | CCCAATAATCCTGAAATT | 73 |
| | Hs00153519_m1 | Forward Primer | CTATAGGCCAGAGTATGCGGTTAAC | 74 |
| | | Reverse Primer | GCAGTGAAAGGCTTCTGAAAACTC | 75 |
| PAX5 | NM_016734 | Probe | CCAGTGGACACTATGC | 76 |
| | Hs00277134_m1 | Forward Primer | CAGTCCCAGCTTCCAGTCACA | 77 |
| | | Reverse Primer | ACGAGCCGGCCGAATC | 78 |

TABLE 2-continued

Primer and probe sequences employed for panel of 36 genes surveyed.

| Gene | Accession No. (Assay I.D. No.)* | | Sequences | SEQ. ID. NO. |
|---|---|---|---|---|
| CD44 | AJ251595.1 | Probe | CAGCCATTCTGGAATT | 79 |
| | (NM_000610) | Forward Primer | GCAAACACAACCTCTGGTCCTATAA | 80 |
| | | Reverse Primer | CCAAGAGGGATGCCAAGATG | 81 |
| HGAL/ | AF521911 | Probe | CCATCCAGGACAATGT | 82 |
| GCET2 | (NM_152785) | Forward Primer | CCCAAAACGAAAATGAAAGAATGT | 83 |
| | (Hs00277164_m1) | Reverse Primer | GGGTATAGCACAGCTCCTCTGAGTA | 84 |
| MYBL1/ | X66087.1 | Probe | CAATTTGACTGAAGATTC | 85 |
| A-MYB | (Hs00277146_m1) | Forward Primer | AACCAAACCCTAACACTTCCAAAG | 86 |
| | | Reverse Primer | TTCTGTCTTCCCATAAACCACTGTT | 87 |
| BCL7A | NM_020993 | Probe | CTGTTTTTGTCATCAACC | 88 |
| | Hs00277139_m1 | Forward Primer | AATCTACAAATGGGTCCCTGTGA | 89 |
| | | Reverse Primer | ACACTTCTCGTCCTTGCCTTTT | 90 |
| PLAU | NM_002658 | Probe | CCTGCCAGGGAGAC | 91 |
| | (Hs00170182_m1) | Forward Primer | TCTGAAGTCACCACCAAAATGCT | 92 |
| | | Reverse Primer | CGGCCTTGGAGGGAACA | 93 |
| NPM3 | NM_006993 | Probe | CTCATCGTAACAATCTG | 94 |
| | (Hs00199625_m1) | Forward Primer | GGCCCTGTGCGGATCAC | 95 |
| | | Reverse Primer | CTCTCCTCCTCAGAAACATCATTG | 96 |
| HLA-DQA1 | NM_002122 | Probe | CACTGGGAGCCTGAG | 97 |
| | (N/A) | Forward Primer | CCTGGACCAGCCTCTTCTGA | 98 |
| | | Reverse Primer | CAGTCTCTGTGAGCTCTGACATAGG | 99 |
| HLA-DRA | NM_019111 | Probe | CATCACCTCCATGTGC | 100 |
| | (Hs00219578_m1) | Forward Primer | GCAAAAGCAATGCAGCAGAAC | 101 |
| | | Reverse Primer | GGATTGTAATATTGCCAGCTTTGTAA | 102 |
| FN1 | NM_002026 | Probe | ATCCAAGCTCAAGTGGTCC | 103 |
| | (Hs00365058_m1) | Forward Primer | CTATGGCCGTGGCATTGG | 104 |
| | | Reverse Primer | GTGGGAGTTGGGCTGACT | 105 |
| EEF1A1L14 | NM_001403 | Probe | CCAAGGCATGTTAGCAC | 106 |
| | (Hs00265885_m1) | Forward Primer | TTTCTGGTTGGAATGGTGACAA | 107 |
| | | Reverse Primer | GGGTGACTTTCCATCCCTTGA | 108 |
| GAPDH | XM_171437 | Probe | CCCTGGTGACCAGGC | 109 |
| | (4326317E) | Forward Primer | AGCCGAGCCACATCGCT | 110 |
| | | Reverse Primer | TGGCAACAATATCCACTTTACCAGAGT | 111 |
| PGK1 | NM_000291 | Probe | AAGGTTAAAGCCGAGCCA | 112 |
| | (4326318E) | Forward Primer | GGGAAAAGATGCTTCTGGGAA | 113 |
| | | Reverse Primer | TTGGAAAGTGAAGCTCGGAAA | 114 |

*Assay I.D. No. of Applied Biosystems, Foster City, CA.

Expression of mRNA for 36 tested genes and 2 endogenous control genes was measured in each DLBCL specimen-with real time PCR using the Applied Biosystems Assays-on-Demand™ Gene Expression Products on an ABI PRISM® 7900HT Sequence Detection System (Applied Biosystems, Foster City, Calif.) as previously reported (Lossos et al., Leukemia 17:789-95, 2003). For each gene, 2-4 assays (TaqMan® probe and primer sets) were tested. The probes contain a 6-carboxy-fluorescein phosphoramidite (FAM™ dye) label at the 5' end and a minor groove binder (MGB) and non-fluorescent quencher (NFQ) at the 3' end, and designed to hybridize across exon junctions. The assays are supplied with primers and probe concentrations of 900 nM and 250 nM, respectively. Real-time assays used in this study had high (near 100%) amplification efficiencies.

No fluorescent signal was generated by these assays when genomic DNA was used as a substrate, validating the assays as measuring mRNA only. The assays were highly reproducible with inter-run variance of less than 0.16 for all the genes. Phosphoglycerate kinase 1 (PGK1) and glyceraldehyde-3-phosphate dehydrogenase (GAPDH) were used as the endogenous RNA/cDNA quantity controls (P/N 4326318E and P/N 4326317E, respectively Applied Biosystems, Foster City, Calif.). We chose PGK1 and GAPDH based on an analysis of their relatively constant expression in DLBCL tumors. Since the normalization to PGK1 and GAPDH endogenous control genes lead to similar results and conclusions, we present only the data normalized to PGK1 expression. For calibration and generation of standard curves we used Raji cDNA and/or cDNA prepared from Universal Human Reference RNA (Stratagene, La Jolla, Calif.). The latter was used for genes with low abundance in Raji cell line (CCND1, CCND2, SLA, NR4A3, CD44, PLAU, and FN1). To control for possible variability between different PCR runs performed on different days, expression of all the analyzed and endogenous control genes was assessed in Raji cell line before, midway and upon completion of the analysis of all the experimental DLBCL specimens. The variance between these 3 runs for all the genes assessed in the Raji cell line was less than 0.16.

Calculation of normalized gene expression values was performed as follows. $C_t$ values measured from tumor samples were converted to quantity of RNA expressed in ng/µl, by referencing to the standard curve for the gene. For each gene the ratio of the quantity expressed to the quantity of expression of the reference gene, GAPDH was then calculated. For each gene, the same ratio was determined for calibrator RNA obtained from Raji cells or from the Universal Standard Reference. Finally, the ratio obtained from the tumor sample was divided by the ratio obtained for the calibrator cells.

Gene expression values for each of the 36 genes and 66 patients is shown in Table 3.

TABLE 3

Normalized Gene Expression Values Determined in Sixty-Six Patients Referenced to GAPDH and Raji Cells Unless Otherwise Indicated

| Gene | Normalized Expression Values | | |
|---|---|---|---|
| | Mean | Variance | Standard Deviation |
| ICAM1/CD54 | 2.26 | 8.16 | 2.86 |
| PMSI | 3.26 | 6.31 | 2.51 |
| p53 | 2.58 | 3.66 | 1.91 |

TABLE 3-continued

Normalized Gene Expression Values Determined in Sixty-Six Patients Referenced to GAPDH and Raji Cells Unless Otherwise Indicated

| Gene | Normalized Expression Values | | |
|---|---|---|---|
| | Mean | Variance | Standard Deviation |
| BCL-2 | 21.23 | 840.02 | 28.98 |
| BIRC5/SURVIVIN | 1.31 | 0.93 | 0.96 |
| PRDM1 | 32.44 | 817.94 | 28.60 |
| BCL-6 | 5.62 | 117.79 | 10.85 |
| CCND1* | 0.78 | 4.04 | 2.01 |
| CCND2* | 4.18 | 57.02 | 7.55 |
| CD38 | 11.01 | 85.15 | 9.23 |
| CR2 | 2.05 | 17.25 | 4.15 |
| Ki-67 | 1.77 | 1.01 | 1.00 |
| IRF4 | 49.66 | 4641.85 | 68.13 |
| MYC | 2.07 | 7.69 | 2.77 |
| PDE4B | 36.30 | 1238.24 | 35.19 |
| PIK3CG | 9.20 | 56.19 | 7.50 |
| SCYA3 | 9.72 | 158.87 | 12.60 |
| SLAM | 1.01 | 1.23 | 1.11 |
| WASPIP | 6.95 | 42.93 | 6.55 |
| CFLAR | 23.53 | 1800.59 | 42.43 |
| LMO2 | 7.34 | 62.07 | 7.88 |
| LRMP | 3.90 | 8.12 | 2.85 |
| SLA* | 108.59 | 23782.23 | 154.21 |
| NR4A3* | 8.41 | 97.50 | 9.87 |
| CD10 | 1.51 | 3.38 | 1.84 |
| PAX5 | 6.46 | 176.48 | 13.28 |
| M17 | 1.87 | 3.11 | 1.76 |
| MYBL1/A-MYB | 3.72 | 17.33 | 4.16 |
| BCL7A | 2.44 | 4.31 | 2.08 |
| CD44 (139)* | 5.13 | 15.53 | 3.94 |
| PLAU* | 6.51 | 99.49 | 9.97 |
| NPM3 | 1.49 | 2.28 | 1.51 |
| HLA-DQA1 | 2.91 | 7.19 | 2.68 |
| EEF1A1L4 | 1.42 | 0.70 | 0.84 |
| HLA-DRA | 4.43 | 11.52 | 3.39 |
| FN1* | 2.46 | 14.57 | 3.82 |

*Referenced to Stratagene Universal Reference RNA.

EXAMPLE 2

This example illustrates the statistical evaluation for developing a survival predictive model.

The normalized gene expression values were log-transformed (base 2) similar to what is done with hybridization array data.

Overall survival time of DLBCL patients was calculated from the date of the diagnosis until death or last follow-up examination. Survival curves were estimated using the product-limit method of Kaplan-Meier and were compared using the log-rank test.

To determine a small list of genes whose expression segregated DLBCL tumors into subgroups with distinct overall survival, we performed a univariate Cox proportional hazards analysis with the overall survival as the dependent variable. Genes with an absolute univariate Cox score >1.5 or <−1.5 were analyzed by a multivariate regression analysis (with and without IPI components) using a Cox proportional hazards regression model with overall survival as the dependent variable. This same model was used to adjust the effects of gene expressions for IPI. p values<0.05 were considered to be significant. Backward stepwise analysis was also used, to find the minimal set of genes that were predictive. A p-value cutoff of 0.05 was used for deletion of model terms.

Results of the univariate analysis are shown in FIG. 1. The genes were ranked based upon their predictive power (univariate score) with negative score associated with longer overall survival while positive univariate score associated with shorter overall survival. Six genes with absolute univariate score >1.5 (LMO2, BCL-6, FN1, CCND2, SCYA3 and BCL-2) were selected for further analysis. On multivariate Cox regression analysis with DLBCL overall survival as a dependent variable, none of these genes independently predicted overall survival at a statistically significant level, however on backward stepwise analysis, expression of LMO2 correlated with DLBCL overall survival (p=0.011). Multivariate Cox regression analysis incorporating all the components of IPI together with the expression of these 6 genes disclosed that only LDH was an independent predictor of DLBCL overall survival (p=0.0038). However, on backward stepwise analysis, both LDH and LMO2 expression were independent predictors of DLBCL overall survival (p=0.0035 and p=0.025, respectively).

Figure 2:
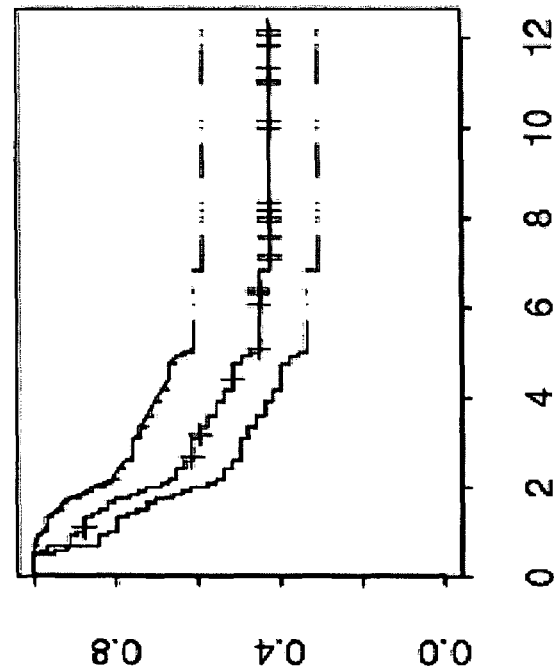
FIG. 2 illustrates the development of the 6 gene model showing (A) Kaplan-Meier estimates of overall survival in the 66 DLBCL cases analyzed by quantitative RT-PCR with TaqMan® probe-based assays in which dotted lines represent 95% confidence intervals and (B) Kaplan-Meier curves of overall survival in the tertiles (low, medium and high) defined by a prediction model based on the weighted expression of 6-genes (LMO2, BCL-6, FN1, CCND2, SCYA3 and BCL-2) in which the significance measures are based on log-likelihood estimates of the p-value, treating the model as a continuous variable or as a class (first and second p-values, respectively).
Figure 2:
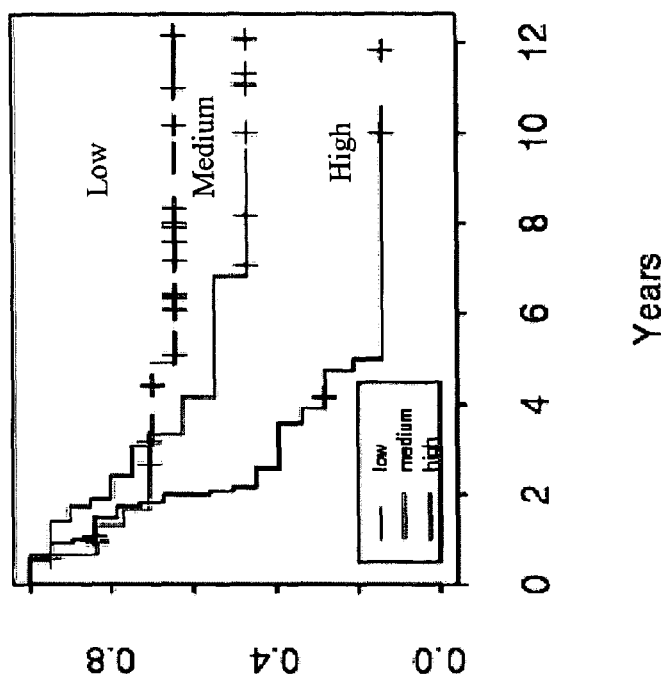

Since this analysis established an inter-correlation between the expressions of these 6 genes and survival, we constructed a model based on a weighted predictor derived from the relative contributions of each gene in the multivariate analysis. The weighted predictor (z) was calculated for each tumor specimen and the tumors were ranked into 3 tertiles: low, medium and high using the −0.63 and 0.093 as cut points (<−0.063—low risk, between −0.063 to <0.093, medium risk and >0.093—high risk groups). The overall survival of these 3 groups was significantly different (p=0.004) with 5-year survival of 65%, 49% and 15% for the low, medium and high groups, respectively (mean overall survival [95% confidence interval] of 7.1 {5.4—not achieved}, 9.0 {1.1—not achieved} and 4.5 {1.2-4.3} years, respectively, FIG. 2). Consequently, patients with tumors expressing high levels of LMO2, BCL-6 and FN1 and low levels of CCND2, SCYA3 and BCL-2, survived longer.

For construction of the survival prediction model, we derived the weighted predictor (Z) from the multivariate analysis for each of the six genes:

$$Z=(-0.0273 \times LMO2)+(-0.2103 \times BCL6)+(-0.1878 \times FN1)+(0.0346 \times CCND2)+(0.1888 \times SCYA3)+(0.5527 \times BCL2).$$

Thus for example the negative weight on LMO2 means that higher expression correlates with lower risk (longer survival). The positive weight on CCND2 means that higher expression correlates with higher risk (shorter survival).

EXAMPLE 3

This example illustrates the validation of the survival prediction model.

Figure 3:
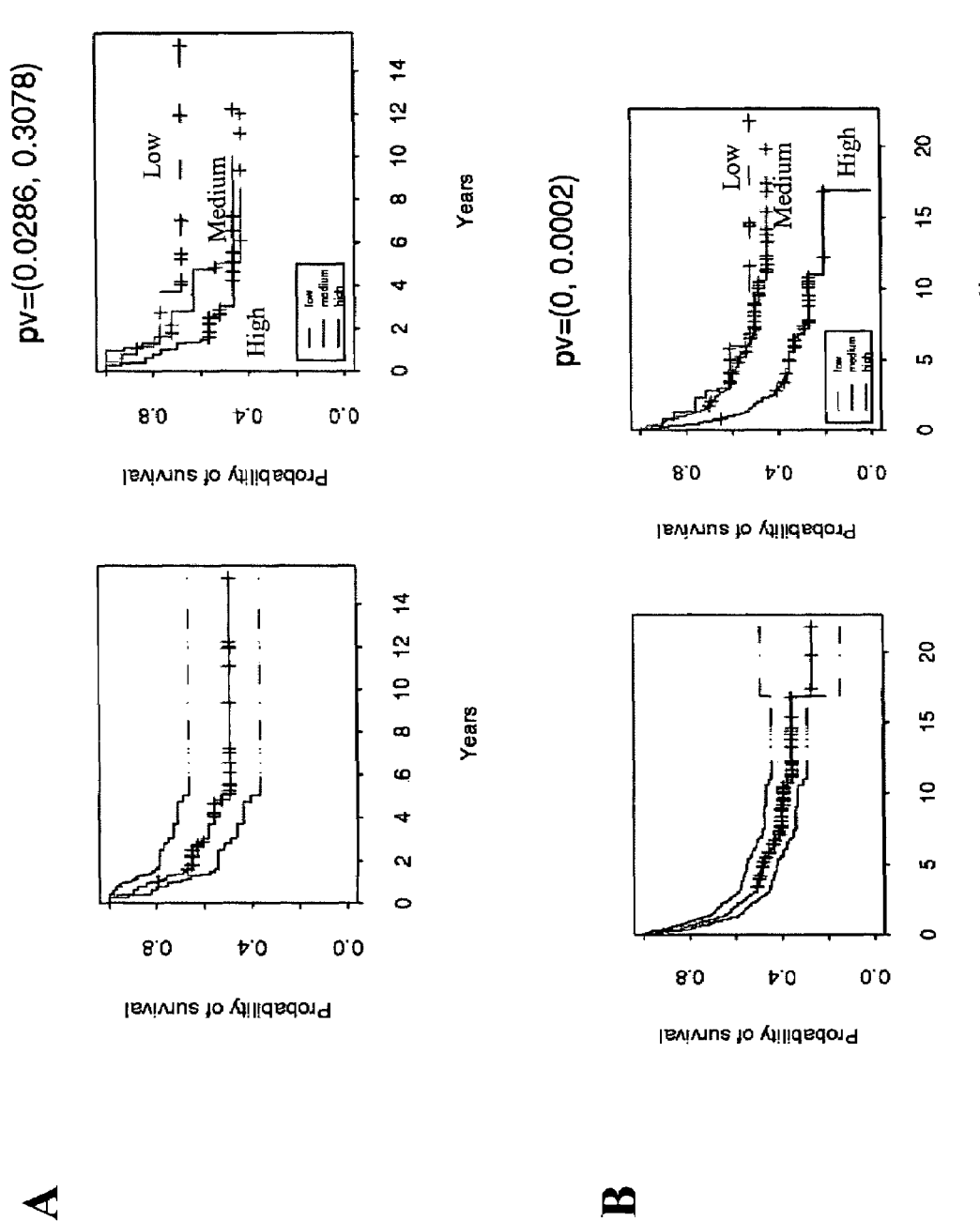
FIG. 3 illustrates the external validation of the performance of the 6-gene model on data from (A) oligonucleotide microarrays showing in the Left panel, Kaplan-Meier estimates of overall survival for the 58 DLBCL cases reported by Shipp et al.(Shipp et al., supra, 2002) in which dotted lines represent 95% confidence intervals and in the right panel, Kaplan-Meier estimates of overall survival of 58 patients when subdivided into tertiles (low, medium and high) using the 6-gene prediction model, the significance measures being based on log-likelihood estimates of the p-value treating the model as a continuous variable or as a class (first and second p-values, respectively) and (B) cDNA microarrays showing a similar analysis of data from the 240 DLBCL cases reported by Rosenwald et al. (Rosenwald et al., supra, 2002).

To validate the usefulness of the model derived in Example 2, the model was applied to two independent previously published DLBCL gene expression data sets derived from DNA microarray methodology (Shipp et al., supra, 2003; Rosenwald et al., supra, 2003). Application of the 6 gene prediction model to data from Shipp et al. (Shipp et al., supra, 2003)(FIG. 3A) and to that of Rosenwald et al. (Rosenwald et al., supra, 2002) (FIG. 3b) confirmed its ability to predict survival since it could stratify DLBCL cases into 3 subgroups with statistically significant different overall survival (P=0.03 and P=0.0004, respectively). Although in the smaller DLBCL cohort reported by Shipp et al., the overall survival of the group in the medium tertile was similar at the 5 year point to that of their high risk tertile, this medium tertile did have an intermediate risk in the larger cohort of patients analyzed by Rosenwald et al. (Rosenwald et al., supra, 2002) (FIG. 3B).

Figure 4:
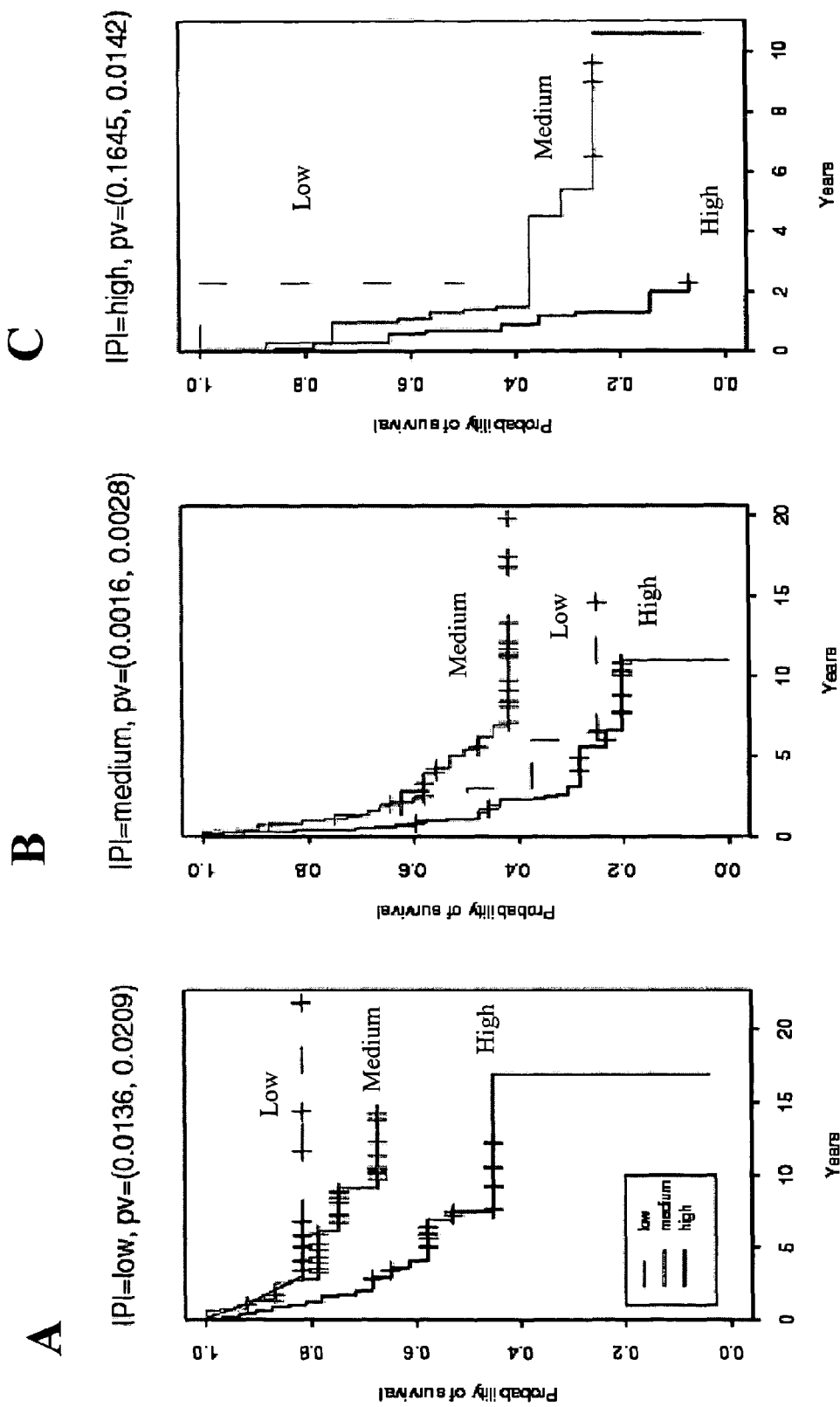
FIG. 4 illustrates the improvement the 6-gene model adds to the International Prognostic Index showing Kaplan-Meier estimates of overall survival for each IPI group (scores 0-1, 2-3, 4-5) of patients reported by Rosenwald et al. (Rosenwald et al., supra, 2002) when subdivided into tertiles (low, medium and high) using the 6-gene prediction model in which the significance measures are based on log-likelihood estimates of the p-value treating the model as a continuous variable or as a class (first and second p-values, respectively) (n=11, 39 and 32 for top, middle and bottom tertiles, respectively, of low IPI score plots; n=8, 48 and 52 for top, middle and bottom tertiles, respectively, of medium IPI score plots and n=2, 16 and 14 for top middle and bottom tertiles, respectively, of high IPI score plots).

We next analyzed whether this prediction model could add to the prognostic value of the IPI. In our own series of 66 patients there were not enough patients in the lowest risk IPI group to achieve statistical significance. But in our patients within the high clinical risk IPI group, the six gene expression model could further subdivide the patients in respect to survival (P=0.006) (data not shown). We, therefore, tested the model on the larger DLBCL data set derived from microarray analysis reported by Rosenwald et al. (Rosenwald et al., supra, 2002) (FIG. 4). We used their same three subdivisions of the patients according to the IPI (low, medium and high risk). Within each of these subgroups we further divided the patients according to the 6 gene expression model. In some of these groups the patients numbers were limited. But in each IPI strata we could identify an especially poor surviving group (FIG. 4 blue lines). By combining the lowest surviving tertiles from the medium and high risk IPI strata, then we identify 30% of all patients that receive very little benefit from current therapy.

The present study defined and validated across the published studies a small set of genes whose expression can predict DLBCL survival and which can be measured by a clinically applicable method. To this end, we evaluated side-by side the prognostic significance of 36 representative genes chosen based on the previous reports suggesting their prognostic potential or from our own analysis of the existing microarray data (Table 1). We have designed a prediction model of overall survival consisting of 6 genes that subdivided DLBCL patients into three prognostic groups in our series of 66 patients and in independent groups of 58 and 240 DLBCL tumors analyzed by Shipp et al. (Shipp et al., supra, 2002) and Rosenwald et al. (Rosenwald et al., supra, 2002), respectively. The validation of our model did not require any adjustments of the published microarray data or any refinements of our gene list. Moreover, this model could further sub-classify DLBCL patients within IPI strata into longer- and shorter-term survivors. The genes comprising this model are present in each of the previously denoted lymphocyte signatures such as germinal (LMO2 and BCL-6), activated B cell (BCL-2, CCND2, SCYA3) and lymph node signatures (FN1) (Alizadeh et al., supra, 2000; Rosenwald et al., supra, 2002). However, the model is independent of these signatures and several genes associated with these signatures do not carry predictive power in our model.

LMO2, BCL-6 and FN1 were the genes whose expression correlated with prolonged survival. LMO2 was first discovered by its homology with the T cell oncogene LMO1 (Boehm et al., *Proc Natl Acad Sci USA* 88:4367-71, 1991). It plays an important role in erythropoiesis and angiogenesis presumably through transcriptional regulation (Warren et al., *Cell* 1994; 78:45-57, 1994; Yamada et al., *Proc Natl Acad Sci USA* 97:320-4, 2000). The LMO2 locus on chromosome 11p13 is the most frequent site of chromosomal translocation in childhood T-cell acute lymphoblastic leukemia (Boehm et al., supra, 1991). LMO2 is expressed in myeloid and erythroid precursors of hematopoietic system and its expression decreases during differentiation. LMO2 expression is low in resting peripheral B cells, however it is markedly increased in GC lymphocytes (Alizadeh et al., supra, 2000). LMO2 is not expressed in normal T lymphocytes, however following chromosomal translocation, its ectopic expression in thymocytes contributes to the leukemogenesis (Royer-Pokora et al., *Oncogene* 6:1887-93, 1991). Interestingly, in two recently observed cases of leukemia complicating retrovirus based gene therapy of X-linked severe combined immunodeficiency, the vector inserted itself near the LMO2 gene (Kaiser, *Science* 299: 495, 2003). Neither the functional significance of increased LMO2 expression in GCB lymphocytes nor its potential role in GCB-derived tumors is known.

The BCL-6 gene, identified by virtue of its involvement in chromosomal translocations affecting band 3q27, encodes a POZ/Zinc finger sequence-specific transcriptional repressor (Chang et al., *Proc Natl Acad Sci USA* 93:6947-52, 1996; Kerckaert et al., *Nat Genet* 1993; 5:66-70, 1993; Seyfert et al., *Oncogene* 1996; 12:2331-42, 1996). The BCL-6 gene is normally expressed in B and $CD4^+$ T cells within the germinal center (GC), and it controls GC formation and T-cell-dependent antigen responses (Cattoretti et al., *Blood* 86:45-53, 1995; Dent et al., *Proc Natl Acad Sci USA* 95:13823-8, 1998; Ye et al., *Nat Genet* 16:161-70, 1997). It is considered one of the hallmarks of the GC and is expressed in NHL whose origin is from GCB lymphocytes. BCL-6 expression was previously reported to predict DLBCL outcome (Lossos et al., *Blood* 98:945-951, 2001).

FN1 is a component of extracellular matrix in the lymph-node signature. Its expression may reflect the response of the lymph node to the tumor cells. Indeed, some cases of DLBCL demonstrate a sclerotic reaction. This gene, together with BCL-6, was included in the survival prediction model constructed by Rosenwald et al. (Rosenwald et al., supra, 2002).

In contrast to these 3 genes, expression of BCL-2, CCND2, SCYA3 correlated with short survival. All of these 3 genes are included in the ABC-like signature (Alizadeh et al., supra, 2000). BCL2 protein expression is down-regulated in normal GCB cells, but is frequently up-regulated in NHL by virtue of t(14;18) translocation (Alizadeh et al., supra, 2000; Kramer et al., *Blood* 92:3152-62). Overexpression of the BCL2 protein is known to prevent apoptosis. High BCL2 protein expression has been repeatedly shown to be an independent poor prognostic indicator for DLBCL (Gascoyne et al., *Blood* 90:244-51, 1997; Kramer et al., *J Clin Oncol* 14:2131-8; Hermine et al., *Blood* 87:265-72, 1996; Hill et al., *Blood* 88:1046-51, 1996).

CCND2 encodes a protein that belongs to the highly conserved cyclin family, whose members are characterized by a dramatic periodicity in protein abundance through cell cycle. This cyclin forms a complex with CDK4 or CDK6 and regulates their activity thus controlling the cell cycle G1/S transition. Consequently, its expression may be associated with higher proliferation rates of the tumors. SCYA3 is a CC chemokine that recruits inflammatory cells, including lymphocytes, monocytes, eosinophils and mast cells to sites of inflammation (Proost et al., *Int J Clin Lab Res* 26:211-23, 1996). Its function in B cell lymphomas is unknown, but it is mainly expressed in the ABC-like group of DLBCL tumors and its expression in lymphocytes can be induced by B cell receptor stimulation (Alizadeh et al., supra, 2000). Interestingly, the promoter regions of both CCND2 and SCYA3 genes contain high-affinity BCL6 binding sites and the expression of these two genes is repressed by BCL6 (Shaffer et al., *Immunity* 13:199-212, 2000). This observation underscores the complex interrelation between the expression of individual genes singularly implicated in DLBCL prognosis (e.g. HGAL) (Lossos et al., *Blood* 101: 433-40, 2003), however not contributing to the model based on multivariate analysis.

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinency of the cited references.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for classifying a patient having diffuse large B-cell lymphoma (DLBCL), the method comprising:
   measuring expression of a plurality of genes in a tumor sample from the patient to produce measured expression values;
   normalizing said measured expression values to produce normalized expression values;
   correlating said normalized expression values to normalized reference expression values obtained for said plurality of genes from DLBCL patients grouped into survival groups; and
   classifying the patient into one of said survival groups based upon weighed predictor Z in formula:

$$Z=(A \times LMO2)+(B \times BCL6)+(C \times FN1)+(D \times CCND2)+(E \times SCYA3)+(F \times BCL2)$$

wherein A is −0.03, B is −0.2, C is −0.2, D is 0.03, E is 0.2, and F is 0.6 and wherein LMO2, BCL6, FN1, CCND2, SCYA3 and BCL2 are log base 2 of normalized expression values for genes LMO2, BCL6, FN1, CCND2, SCYA3 and BCL2, respectively.

2. The method according to claim 1 wherein a Z value of less than −0.06 indicates high probability of survival, a Z value of from −0.06 to 0.09 indicates medium probability of survival and a Z value of greater than 0.09 indicates low probability of survival.

3. The method according to claim 1, further comprising:
   predicting survival of the patient wherein said plurality of genes are predictive of probability of survival and wherein said survival groups comprise groups of said DLBCL patients having known overall probability of survival.

4. The method according to claim 3 wherein said known overall probability of survival comprises overall probability of survival after anthracycline-based chemotherapy.

5. The method according to claim 1 wherein said normalized expression values comprise ratios of measured expression values obtained from said plurality of genes to expression values of a housekeeping gene.

6. The method according to claim 5 wherein the housekeeping gene is PGK1 or GAPDH.

7. The method according to claim 1 wherein said measuring expression of said plurality of genes in said tumor sample from the patient comprises performing real time RT-PCR on a portion of said tumor sample from the patient.

8. The method according to claim 1, further comprising:
   determining whether said normalized expression values are similar to said normalized reference expression values obtained for said plurality of genes grouped into said survival groups selected from low, medium and high overall probability of survival after anthracycline-based chemotherapy.

9. The method according to claim 1 wherein said plurality of genes is selected from the group consisting of LMO2, BCL6, FN1, CCND2, SCYA3 and BCL2.

10. The method according to claim 1 wherein said plurality of genes comprises LMO2, BCL6, FN1, CCND2, SCYA3 and BCL2.

11. The method according to claim 1 wherein said measuring expression of a plurality of genes comprises:
    hybridizing a plurality of primers to said plurality of genes, said plurality of primers being selected from a group consisting of SEQ. ID. NO. 11, SEQ. ID. NO. 12, SEQ. ID. NO. 20, SEQ. ID. NO. 21, SEQ. ID. NO. 26, SEQ. ID. NO. 27, SEQ. ID. NO. 50, SEQ. ID. NO. 51, SEQ. ID. NO. 62, SEQ. ID. NO. 63, SEQ. ID. NO. 104, and SEQ. ID. NO. 105.

* * * * *

UNITED STATES PATENT AND TRADEMARK OFFICE
CERTIFICATE OF CORRECTION

| | | |
|---|---|---|
| PATENT NO. | : 7,332,280 B2 | Page 1 of 1 |
| APPLICATION NO. | : 10/792374 | |
| DATED | : February 19, 2008 | |
| INVENTOR(S) | : Levy et al. | |

It is certified that error appears in the above-identified patent and that said Letters Patent is hereby corrected as shown below:

In The Specification Under Column 1:

• Please replace lines 13-21 with:

-- FEDERALLY-SPONSORED RESEARCH OR DEVELOPMENT
This invention was made with Government support under contracts CA034233 and CA033399 awarded by the National Institutes of Health. The Government has certain rights in this invention. --

Signed and Sealed this
Nineteenth Day of April, 2011

David J. Kappos
*Director of the United States Patent and Trademark Office*

SEQUENCE LISTING

```
<160> NUMBER OF SEQ ID NOS: 114

<210> SEQ ID NO 1
<211> LENGTH: 16
<212> TYPE: DNA
<213> ORGANISM: Homo sapiens

<400> SEQUENCE: 1
ctgttcccag gacctg                                                       16

<210> SEQ ID NO 2
<211> LENGTH: 22
<212> TYPE: DNA
<213> ORGANISM: Homo sapiens

<400> SEQUENCE: 2
acgctgagct cctctgctac tc                                                22

<210> SEQ ID NO 3
<211> LENGTH: 20
<212> TYPE: DNA
<213> ORGANISM: Homo sapiens
```

-continued

```
<400> SEQUENCE: 3
cacagatgtc tgggcattgc                                              20

<210> SEQ ID NO 4
<211> LENGTH: 19
<212> TYPE: DNA
<213> ORGANISM: Homo sapiens

<400> SEQUENCE: 4
catagttctc cagtttaac                                               19

<210> SEQ ID NO 5
<211> LENGTH: 18
<212> TYPE: DNA
<213> ORGANISM: Homo sapiens

<400> SEQUENCE: 5
tggatgctgg tgccacaa                                                18

<210> SEQ ID NO 6
<211> LENGTH: 25
<212> TYPE: DNA
<213> ORGANISM: Homo sapiens

<400> SEQUENCE: 6
cgttatctcg cacctcaatt ttatc                                        25

<210> SEQ ID NO 7
<211> LENGTH: 14
<212> TYPE: DNA
<213> ORGANISM: Homo sapiens

<400> SEQUENCE: 7
ctggctgcca atcc                                                    14

<210> SEQ ID NO 8
<211> LENGTH: 19
<212> TYPE: DNA
<213> ORGANISM: Homo sapiens

<400> SEQUENCE: 8
gctttccacg acggtgaca                                               19

<210> SEQ ID NO 9
<211> LENGTH: 18
<212> TYPE: DNA
<213> ORGANISM: Homo sapiens

<400> SEQUENCE: 9
tgactgcggc tcctccat                                                18

<210> SEQ ID NO 10
<211> LENGTH: 17
<212> TYPE: DNA
<213> ORGANISM: Homo sapiens

<400> SEQUENCE: 10
acaaaggcat cccagcc                                                 17

<210> SEQ ID NO 11
<211> LENGTH: 19
<212> TYPE: DNA
<213> ORGANISM: Homo sapiens
```

<400> SEQUENCE: 11
acctgcacac ctggatcca                                                19

<210> SEQ ID NO 12
<211> LENGTH: 23
<212> TYPE: DNA
<213> ORGANISM: Homo sapiens

<400> SEQUENCE: 12
acagccagga gaaatcaaac aga                                           23

<210> SEQ ID NO 13
<211> LENGTH: 14
<212> TYPE: DNA
<213> ORGANISM: Homo sapiens

<400> SEQUENCE: 13
cctttgcaat tttg                                                     14

<210> SEQ ID NO 14
<211> LENGTH: 23
<212> TYPE: DNA
<213> ORGANISM: Homo sapiens

<400> SEQUENCE: 14
ctggacagag aaagagccaa gaa                                           23

<210> SEQ ID NO 15
<211> LENGTH: 17
<212> TYPE: DNA
<213> ORGANISM: Homo sapiens

<400> SEQUENCE: 15
ggcacggcgc actttct                                                  17

<210> SEQ ID NO 16
<211> LENGTH: 18
<212> TYPE: DNA
<213> ORGANISM: Homo sapiens

<400> SEQUENCE: 16
tgaatctcac acaaacac                                                 18

<210> SEQ ID NO 17
<211> LENGTH: 18
<212> TYPE: DNA
<213> ORGANISM: Homo sapiens

<400> SEQUENCE: 17
cccggagagc tgacaatg                                                 18

<210> SEQ ID NO 18
<211> LENGTH: 23
<212> TYPE: DNA
<213> ORGANISM: Homo sapiens

<400> SEQUENCE: 18
tcagtgctcg gttgctttag act                                           23

<210> SEQ ID NO 19
<211> LENGTH: 19
<212> TYPE: DNA

<213> ORGANISM: Homo sapiens

<400> SEQUENCE: 19
ccttaccatt gtgagaagt                                                        19

<210> SEQ ID NO 20
<211> LENGTH: 21
<212> TYPE: DNA
<213> ORGANISM: Homo sapiens

<400> SEQUENCE: 20
gcgaatccac acaggagaga a                                                     21

<210> SEQ ID NO 21
<211> LENGTH: 22
<212> TYPE: DNA
<213> ORGANISM: Homo sapiens

<400> SEQUENCE: 21
ttgtgacgga aatgcaggtt ac                                                    22

<210> SEQ ID NO 22
<211> LENGTH: 16
<212> TYPE: DNA
<213> ORGANISM: Homo sapiens

<400> SEQUENCE: 22
tccatttgca gcagct                                                           16

<210> SEQ ID NO 23
<211> LENGTH: 22
<212> TYPE: DNA
<213> ORGANISM: Homo sapiens

<400> SEQUENCE: 23
ccgagaagct gtgcatctac ac                                                    22

<210> SEQ ID NO 24
<211> LENGTH: 22
<212> TYPE: DNA
<213> ORGANISM: Homo sapiens

<400> SEQUENCE: 24
aggttccact tgagcttgtt ca                                                    22

<210> SEQ ID NO 25
<211> LENGTH: 16
<212> TYPE: DNA
<213> ORGANISM: Homo sapiens

<400> SEQUENCE: 25
acagacctcc agcatc                                                           16

<210> SEQ ID NO 26
<211> LENGTH: 20
<212> TYPE: DNA
<213> ORGANISM: Homo sapiens

<400> SEQUENCE: 26
ccctacatgc gcagaatggt                                                       20

<210> SEQ ID NO 27
<211> LENGTH: 24

<212> TYPE: DNA
<213> ORGANISM: Homo sapiens

<400> SEQUENCE: 27
gacctcttct tcgcacttct gttc                                          24

<210> SEQ ID NO 28
<211> LENGTH: 15
<212> TYPE: DNA
<213> ORGANISM: Homo sapiens

<400> SEQUENCE: 28
cttctgcaaa cctgc                                                    15

<210> SEQ ID NO 29
<211> LENGTH: 21
<212> TYPE: DNA
<213> ORGANISM: Homo sapiens

<400> SEQUENCE: 29
ggagaaagga ctgcagcaac a                                             21

<210> SEQ ID NO 30
<211> LENGTH: 22
<212> TYPE: DNA
<213> ORGANISM: Homo sapiens

<400> SEQUENCE: 30
agcatcacat ggaccacatc ac                                            22

<210> SEQ ID NO 31
<211> LENGTH: 16
<212> TYPE: DNA
<213> ORGANISM: Homo sapiens

<400> SEQUENCE: 31
aggcacacac cagttt                                                   16

<210> SEQ ID NO 32
<211> LENGTH: 21
<212> TYPE: DNA
<213> ORGANISM: Homo sapiens

<400> SEQUENCE: 32
ccagccagct gatcagaaga c                                             21

<210> SEQ ID NO 33
<211> LENGTH: 20
<212> TYPE: DNA
<213> ORGANISM: Homo sapiens

<400> SEQUENCE: 33
tccgctgaat tccaagcaat                                               20

<210> SEQ ID NO 34
<211> LENGTH: 18
<212> TYPE: DNA
<213> ORGANISM: Homo sapiens

<400> SEQUENCE: 34
cactctcatc agggtcag                                                 18

<210> SEQ ID NO 35

```
<211> LENGTH: 25
<212> TYPE: DNA
<213> ORGANISM: Homo sapiens

<400> SEQUENCE: 35
cgtcgtgtct caagatctag cttct                                              25

<210> SEQ ID NO 36
<211> LENGTH: 21
<212> TYPE: DNA
<213> ORGANISM: Homo sapiens

<400> SEQUENCE: 36
ggacacacgc cttcttttca a                                                  21

<210> SEQ ID NO 37
<211> LENGTH: 14
<212> TYPE: DNA
<213> ORGANISM: Homo sapiens

<400> SEQUENCE: 37
cccagcaggt tcac                                                          14

<210> SEQ ID NO 38
<211> LENGTH: 23
<212> TYPE: DNA
<213> ORGANISM: Homo sapiens

<400> SEQUENCE: 38
ctacaccatg acaacgcctt acc                                                23

<210> SEQ ID NO 39
<211> LENGTH: 19
<212> TYPE: DNA
<213> ORGANISM: Homo sapiens

<400> SEQUENCE: 39
ggctgatccg ggacgtagt                                                     19

<210> SEQ ID NO 40
<211> LENGTH: 16
<212> TYPE: DNA
<213> ORGANISM: Homo sapiens

<400> SEQUENCE: 40
tcctcctcag agtcgc                                                        16

<210> SEQ ID NO 41
<211> LENGTH: 18
<212> TYPE: DNA
<213> ORGANISM: Homo sapiens

<400> SEQUENCE: 41
cccctggtgc tccatgag                                                      18

<210> SEQ ID NO 42
<211> LENGTH: 20
<212> TYPE: DNA
<213> ORGANISM: Homo sapiens

<400> SEQUENCE: 42
gcctgcctct tttccacaga                                                    20
```

```
<210> SEQ ID NO 43
<211> LENGTH: 16
<212> TYPE: DNA
<213> ORGANISM: Homo sapiens

<400> SEQUENCE: 43
tcgcattcag gtcctt                                                    16

<210> SEQ ID NO 44
<211> LENGTH: 25
<212> TYPE: DNA
<213> ORGANISM: Homo sapiens

<400> SEQUENCE: 44
caggcgttct tctcctagac aacta                                          25

<210> SEQ ID NO 45
<211> LENGTH: 23
<212> TYPE: DNA
<213> ORGANISM: Homo sapiens

<400> SEQUENCE: 45
ggtctgcaca gtgtaccatg ttg                                            23

<210> SEQ ID NO 46
<211> LENGTH: 15
<212> TYPE: DNA
<213> ORGANISM: Homo sapiens

<400> SEQUENCE: 46
atgtcctgaa atttc                                                     15

<210> SEQ ID NO 47
<211> LENGTH: 23
<212> TYPE: DNA
<213> ORGANISM: Homo sapiens

<400> SEQUENCE: 47
ggaaagaaga caagcccaca ctt                                            23

<210> SEQ ID NO 48
<211> LENGTH: 24
<212> TYPE: DNA
<213> ORGANISM: Homo sapiens

<400> SEQUENCE: 48
gtgatgacga agggctagat aagc                                           24

<210> SEQ ID NO 49
<211> LENGTH: 16
<212> TYPE: DNA
<213> ORGANISM: Homo sapiens

<400> SEQUENCE: 49
ctgcatcact tgctgc                                                    16

<210> SEQ ID NO 50
<211> LENGTH: 22
<212> TYPE: DNA
<213> ORGANISM: Homo sapiens

<400> SEQUENCE: 50
atggctctct gcaaccagtt ct                                             22
```

```
<210> SEQ ID NO 51
<211> LENGTH: 15
<212> TYPE: DNA
<213> ORGANISM: Homo sapiens

<400> SEQUENCE: 51
gcggtcggcg tgtca                                                   15

<210> SEQ ID NO 52
<211> LENGTH: 15
<212> TYPE: DNA
<213> ORGANISM: Homo sapiens

<400> SEQUENCE: 52
acctgctcat aaagc                                                   15

<210> SEQ ID NO 53
<211> LENGTH: 19
<212> TYPE: DNA
<213> ORGANISM: Homo sapiens

<400> SEQUENCE: 53
cgcttttgcc tgcagttga                                               19

<210> SEQ ID NO 54
<211> LENGTH: 24
<212> TYPE: DNA
<213> ORGANISM: Homo sapiens

<400> SEQUENCE: 54
cgttctcctg ggtcttgttt aaaa                                         24

<210> SEQ ID NO 55
<211> LENGTH: 17
<212> TYPE: DNA
<213> ORGANISM: Homo sapiens

<400> SEQUENCE: 55
ctccagaatc attatcc                                                 17

<210> SEQ ID NO 56
<211> LENGTH: 19
<212> TYPE: DNA
<213> ORGANISM: Homo sapiens

<400> SEQUENCE: 56
tgagatccac ggccaacag                                               19

<210> SEQ ID NO 57
<211> LENGTH: 18
<212> TYPE: DNA
<213> ORGANISM: Homo sapiens

<400> SEQUENCE: 57
ctcccggtgg caacaatg                                                18

<210> SEQ ID NO 58
<211> LENGTH: 16
<212> TYPE: DNA
<213> ORGANISM: Homo sapiens

<400> SEQUENCE: 58
agacagagct tcttcg                                                  16
```

<210> SEQ ID NO 59
<211> LENGTH: 22
<212> TYPE: DNA
<213> ORGANISM: Homo sapiens

<400> SEQUENCE: 59
tgcctgataa tcgattgcat tg                                    22

<210> SEQ ID NO 60
<211> LENGTH: 21
<212> TYPE: DNA
<213> ORGANISM: Homo sapiens

<400> SEQUENCE: 60
cccagggaag tgaaggtgtc t                                     21

<210> SEQ ID NO 61
<211> LENGTH: 18
<212> TYPE: DNA
<213> ORGANISM: Homo sapiens

<400> SEQUENCE: 61
agactatctc aggctttt                                         18

<210> SEQ ID NO 62
<211> LENGTH: 18
<212> TYPE: DNA
<213> ORGANISM: Homo sapiens

<400> SEQUENCE: 62
caaactgggc cggaagct                                         18

<210> SEQ ID NO 63
<211> LENGTH: 19
<212> TYPE: DNA
<213> ORGANISM: Homo sapiens

<400> SEQUENCE: 63
atgcgcagag accgtcttg                                        19

<210> SEQ ID NO 64
<211> LENGTH: 18
<212> TYPE: DNA
<213> ORGANISM: Homo sapiens

<400> SEQUENCE: 64
aaagcttctt cagtttcc                                         18

<210> SEQ ID NO 65
<211> LENGTH: 19
<212> TYPE: DNA
<213> ORGANISM: Homo sapiens

<400> SEQUENCE: 65
gccaggcact tcagcagaa                                        19

<210> SEQ ID NO 66
<211> LENGTH: 25
<212> TYPE: DNA
<213> ORGANISM: Homo sapiens

<400> SEQUENCE: 66

-continued ggacagggaa tcatagtgag gaaat         25

<210> SEQ ID NO 67
<211> LENGTH: 16
<212> TYPE: DNA
<213> ORGANISM: Homo sapiens

<400> SEQUENCE: 67
cctgcagtct ggacac         16

<210> SEQ ID NO 68
<211> LENGTH: 22
<212> TYPE: DNA
<213> ORGANISM: Homo sapiens

<400> SEQUENCE: 68
tcaccttgcg tcagaagact gt         22

<210> SEQ ID NO 69
<211> LENGTH: 19
<212> TYPE: DNA
<213> ORGANISM: Homo sapiens

<400> SEQUENCE: 69
cccaagcggg ttctctgtt         19

<210> SEQ ID NO 70
<211> LENGTH: 17
<212> TYPE: DNA
<213> ORGANISM: Homo sapiens

<400> SEQUENCE: 70
catgatcaca gaaagac         17

<210> SEQ ID NO 71
<211> LENGTH: 19
<212> TYPE: DNA
<213> ORGANISM: Homo sapiens

<400> SEQUENCE: 71
gcctgcctgt cagcactga         19

<210> SEQ ID NO 72
<211> LENGTH: 25
<212> TYPE: DNA
<213> ORGANISM: Homo sapiens

<400> SEQUENCE: 72
gctcttcgac tctctttggt tcttt         25

<210> SEQ ID NO 73
<211> LENGTH: 18
<212> TYPE: DNA
<213> ORGANISM: Homo sapiens

<400> SEQUENCE: 73
cccaataatc ctgaaatt         18

<210> SEQ ID NO 74
<211> LENGTH: 25
<212> TYPE: DNA
<213> ORGANISM: Homo sapiens

<400> SEQUENCE: 74

```
ctataggcca gagtatgcgg ttaac                                          25

<210> SEQ ID NO 75
<211> LENGTH: 24
<212> TYPE: DNA
<213> ORGANISM: Homo sapiens

<400> SEQUENCE: 75
gcagtgaaag gcttctgaaa actc                                           24

<210> SEQ ID NO 76
<211> LENGTH: 16
<212> TYPE: DNA
<213> ORGANISM: Homo sapiens

<400> SEQUENCE: 76
ccagtggaca ctatgc                                                    16

<210> SEQ ID NO 77
<211> LENGTH: 21
<212> TYPE: DNA
<213> ORGANISM: Homo sapiens

<400> SEQUENCE: 77
cagtcccagc ttccagtcac a                                              21

<210> SEQ ID NO 78
<211> LENGTH: 16
<212> TYPE: DNA
<213> ORGANISM: Homo sapiens

<400> SEQUENCE: 78
acgagccggc cgaatc                                                    16

<210> SEQ ID NO 79
<211> LENGTH: 16
<212> TYPE: DNA
<213> ORGANISM: Homo sapiens

<400> SEQUENCE: 79
cagccattct ggaatt                                                    16

<210> SEQ ID NO 80
<211> LENGTH: 25
<212> TYPE: DNA
<213> ORGANISM: Homo sapiens

<400> SEQUENCE: 80
gcaaacacaa cctctggtcc tataa                                          25

<210> SEQ ID NO 81
<211> LENGTH: 20
<212> TYPE: DNA
<213> ORGANISM: Homo sapiens

<400> SEQUENCE: 81
ccaagaggga tgccaagatg                                                20

<210> SEQ ID NO 82
<211> LENGTH: 16
<212> TYPE: DNA
<213> ORGANISM: Homo sapiens
```

<400> SEQUENCE: 82
ccatccagga caatgt                                                              16

<210> SEQ ID NO 83
<211> LENGTH: 24
<212> TYPE: DNA
<213> ORGANISM: Homo sapiens

<400> SEQUENCE: 83
cccaaaacga aaatgaaaga atgt                                                     24

<210> SEQ ID NO 84
<211> LENGTH: 25
<212> TYPE: DNA
<213> ORGANISM: Homo sapiens

<400> SEQUENCE: 84
gggtatagca cagctcctct gagta                                                    25

<210> SEQ ID NO 85
<211> LENGTH: 18
<212> TYPE: DNA
<213> ORGANISM: Homo sapiens

<400> SEQUENCE: 85
caatttgact gaagattc                                                            18

<210> SEQ ID NO 86
<211> LENGTH: 24
<212> TYPE: DNA
<213> ORGANISM: Homo sapiens

<400> SEQUENCE: 86
aaccaaaccc taacacttcc aaag                                                     24

<210> SEQ ID NO 87
<211> LENGTH: 25
<212> TYPE: DNA
<213> ORGANISM: Homo sapiens

<400> SEQUENCE: 87
ttctgtcttc ccataaacca ctgtt                                                    25

<210> SEQ ID NO 88
<211> LENGTH: 19
<212> TYPE: DNA
<213> ORGANISM: Homo sapiens

<400> SEQUENCE: 88
cttgtttttg tcatcaacc                                                           19

<210> SEQ ID NO 89
<211> LENGTH: 23
<212> TYPE: DNA
<213> ORGANISM: Homo sapiens

<400> SEQUENCE: 89
aatctacaaa tgggtccctg tga                                                      23

<210> SEQ ID NO 90
<211> LENGTH: 22
<212> TYPE: DNA
<213> ORGANISM: Homo sapiens

```
<400> SEQUENCE: 90
acacttctcg tccttgcctt tt                                              22

<210> SEQ ID NO 91
<211> LENGTH: 14
<212> TYPE: DNA
<213> ORGANISM: Homo sapiens

<400> SEQUENCE: 91
cctgccaggg agac                                                       14

<210> SEQ ID NO 92
<211> LENGTH: 23
<212> TYPE: DNA
<213> ORGANISM: Homo sapiens

<400> SEQUENCE: 92
tctgaagtca ccaccaaaat gct                                             23

<210> SEQ ID NO 93
<211> LENGTH: 17
<212> TYPE: DNA
<213> ORGANISM: Homo sapiens

<400> SEQUENCE: 93
cggccttgga gggaaca                                                    17

<210> SEQ ID NO 94
<211> LENGTH: 17
<212> TYPE: DNA
<213> ORGANISM: Homo sapiens

<400> SEQUENCE: 94
ctcatcgtaa caatctg                                                    17

<210> SEQ ID NO 95
<211> LENGTH: 17
<212> TYPE: DNA
<213> ORGANISM: Homo sapiens

<400> SEQUENCE: 95
ggccctgtgc ggatcac                                                    17

<210> SEQ ID NO 96
<211> LENGTH: 24
<212> TYPE: DNA
<213> ORGANISM: Homo sapiens

<400> SEQUENCE: 96
ctctcctcct cagaaacatc attg                                            24

<210> SEQ ID NO 97
<211> LENGTH: 15
<212> TYPE: DNA
<213> ORGANISM: Homo sapiens

<400> SEQUENCE: 97
cactgggagc ctgag                                                      15

<210> SEQ ID NO 98
<211> LENGTH: 20
<212> TYPE: DNA
```

<213> ORGANISM: Homo sapiens

<400> SEQUENCE: 98
cctggaccag cctcttctga                                               20

<210> SEQ ID NO 99
<211> LENGTH: 25
<212> TYPE: DNA
<213> ORGANISM: Homo sapiens

<400> SEQUENCE: 99
cagtctctgt gagctctgac atagg                                         25

<210> SEQ ID NO 100
<211> LENGTH: 16
<212> TYPE: DNA
<213> ORGANISM: Homo sapiens

<400> SEQUENCE: 100
catcacctcc atgtgc                                                   16

<210> SEQ ID NO 101
<211> LENGTH: 21
<212> TYPE: DNA
<213> ORGANISM: Homo sapiens

<400> SEQUENCE: 101
gcaaaagcaa tgcagcagaa c                                             21

<210> SEQ ID NO 102
<211> LENGTH: 26
<212> TYPE: DNA
<213> ORGANISM: Homo sapiens

<400> SEQUENCE: 102
ggattgtaat attgccagct ttgtaa                                        26

<210> SEQ ID NO 103
<211> LENGTH: 19
<212> TYPE: DNA
<213> ORGANISM: Homo sapiens

<400> SEQUENCE: 103
atccaagctc aagtggtcc                                                19

<210> SEQ ID NO 104
<211> LENGTH: 18
<212> TYPE: DNA
<213> ORGANISM: Homo sapiens

<400> SEQUENCE: 104
ctatggccgt ggcattgg                                                 18

<210> SEQ ID NO 105
<211> LENGTH: 18
<212> TYPE: DNA
<213> ORGANISM: Homo sapiens

<400> SEQUENCE: 105
gtgggagttg ggctgact                                                 18

<210> SEQ ID NO 106
<211> LENGTH: 17

```
<212> TYPE: DNA
<213> ORGANISM: Homo sapiens

<400> SEQUENCE: 106
ccaaggcatg ttagcac                                                   17

<210> SEQ ID NO 107
<211> LENGTH: 22
<212> TYPE: DNA
<213> ORGANISM: Homo sapiens

<400> SEQUENCE: 107
tttctggttg gaatggtgac aa                                             22

<210> SEQ ID NO 108
<211> LENGTH: 21
<212> TYPE: DNA
<213> ORGANISM: Homo sapiens

<400> SEQUENCE: 108
gggtgacttt ccatcccttg a                                              21

<210> SEQ ID NO 109
<211> LENGTH: 15
<212> TYPE: DNA
<213> ORGANISM: Homo sapiens

<400> SEQUENCE: 109
ccctggtgac caggc                                                     15

<210> SEQ ID NO 110
<211> LENGTH: 17
<212> TYPE: DNA
<213> ORGANISM: Homo sapiens

<400> SEQUENCE: 110
agccgagcca catcgct                                                   17

<210> SEQ ID NO 111
<211> LENGTH: 27
<212> TYPE: DNA
<213> ORGANISM: Homo sapiens

<400> SEQUENCE: 111
tggcaacaat atccacttta ccagagt                                        27

<210> SEQ ID NO 112
<211> LENGTH: 18
<212> TYPE: DNA
<213> ORGANISM: Homo sapiens

<400> SEQUENCE: 112
aaggttaaag ccgagcca                                                  18

<210> SEQ ID NO 113
<211> LENGTH: 21
<212> TYPE: DNA
<213> ORGANISM: Homo sapiens

<400> SEQUENCE: 113
gggaaaagat gcttctggga a                                              21

<210> SEQ ID NO 114
```

```
<211> LENGTH: 21
<212> TYPE: DNA
<213> ORGANISM: Homo sapiens

<400> SEQUENCE: 114
ttggaaagtg aagctcggaa a                                          21
```